United States Patent
Mihan et al.

(10) Patent No.: US 7,868,108 B2
(45) Date of Patent: Jan. 11, 2011

(54) TRANSITION METAL COMPOUND, LIGAND SYSTEM, CATALYST SYSTEM AND PROCESS FOR PREPARING POLYOLEFINS

(75) Inventors: Shahram Mihan, Bad Soden (DE); Benno Bildstein, Innsbruck (AT); Alexander Solchinger, Norwich (GB); Lars Kölling, Mannheim (DE)

(73) Assignee: Basell Polyolefine GmbH, Wesseling (DE)

( * ) Notice: Subject to any disclaimer, the term of this patent is extended or adjusted under 35 U.S.C. 154(b) by 304 days.

(21) Appl. No.: 12/085,611

(22) PCT Filed: Nov. 27, 2006

(86) PCT No.: PCT/EP2006/011343
§ 371 (c)(1), (2), (4) Date: May 28, 2008

(87) PCT Pub. No.: WO2007/062790
PCT Pub. Date: Jun. 7, 2007

(65) Prior Publication Data
US 2009/0156768 A1    Jun. 18, 2009

Related U.S. Application Data

(60) Provisional application No. 60/753,272, filed on Dec. 22, 2005.

(30) Foreign Application Priority Data
Nov. 30, 2005 (DE) ........................ 10 2005 057 559

(51) Int. Cl.
C08F 4/70 (2006.01)
C08F 4/80 (2006.01)
C07F 15/00 (2006.01)

(52) U.S. Cl. .................. 526/172; 526/169.1; 526/526; 526/161; 526/348; 502/103; 556/138

(58) Field of Classification Search .............. 526/172, 526/161, 169.1; 556/138; 502/103
See application file for complete search history.

(56) References Cited

U.S. PATENT DOCUMENTS

| 4,461,873 | A | 7/1984 | Bailey et al. | 525/240 |
|---|---|---|---|---|
| 5,382,630 | A | 1/1995 | Stehling et al. | 525/240 |
| 5,530,065 | A | 6/1996 | Farley et al. | 525/240 |
| 5,707,751 | A | 1/1998 | Garza et al. | 428/515 |
| 5,852,145 | A | 12/1998 | McLain et al. | 526/133 |
| 6,034,259 | A | 3/2000 | Brookhart et al. | 556/137 |
| 6,087,291 | A | 7/2000 | Speca et al. | 502/104 |
| 6,350,814 | B1 | 2/2002 | Bauer et al. | 525/191 |
| 6,369,177 | B1 | 4/2002 | Tohi et al. | 526/172 |
| 6,417,302 | B1 | 7/2002 | Bohnen | 526/160 |
| 6,437,161 | B1 | 8/2002 | Mihan et al. | 556/11 |
| 6,548,672 | B1 | 4/2003 | Gibson et al. | 546/12 |
| 6,589,905 | B1 | 7/2003 | Fischer et al. | 502/300 |
| 7,002,013 | B1* | 2/2006 | Chi et al. | 546/10 |
| 7,053,160 | B1 | 5/2006 | Bingel et al. | 526/170 |
| 2002/0055600 | A1 | 5/2002 | Fujita et al. | 526/339 |
| 2004/0171774 | A1* | 9/2004 | Rieger et al. | 526/161 |
| 2007/0004884 | A1 | 1/2007 | Bildstein | 526/172 |
| 2007/0173400 | A1 | 7/2007 | Severn et al. | 502/200 |

FOREIGN PATENT DOCUMENTS

| EP | 0 416 815 | 8/1990 |
|---|---|---|
| EP | 0 420 436 | 9/1990 |
| EP | 1 357 134 | 2/1998 |
| WO | WO 91/09882 | 7/1991 |
| WO | WO 95/27005 | 10/1995 |
| WO | WO 98/27124 | 6/1998 |
| WO | WO 98/40419 | 9/1998 |
| WO | EP2006/011343 | 5/2007 |

OTHER PUBLICATIONS

Potvin et al., J. Am. Chem. Soc., 2003, 125, 4894-4906.*
Jairam et al., J. Inorg. Biochem., 2001, 84, 113-118.*
Jens C. Roder et al., "An unusual hexanickel cage complete with . mu.- and .mu.3-chloro bridges and an interstitial .mu.6-chloride," *Chemical Communications*, 2001, 2176-2177, ISSN: 1359-7345, 2001, XP008078296.
G. J. P. Britovsek et al., "Examples of highly active non-metallocene olefin polymerization catalysts across the transition series," *Angewandte. Chemie Int. Ed.* 1999, 38,428.
DATABASE CAPLUS (Online), "Aromatic semicarbazones and harmless agrochemical insecticides containing them," *Chemical Abstracts Service*, Columbus, Ohio, US; Santa, Takeshi et al. , XP002431215 & JP 09 328463 A (Nissan Chemical Industries, LTD., Japan Nissan Chemical Industries, LT) Dec. 22, 1997. (See International Search Report for PCT/EP2006/011343 attached.).

(Continued)

*Primary Examiner*—Rip A. Lee
(74) *Attorney, Agent, or Firm*—Shao-Hua Guo

(57) ABSTRACT

The present invention relates to transition metal compounds of the formula (I),

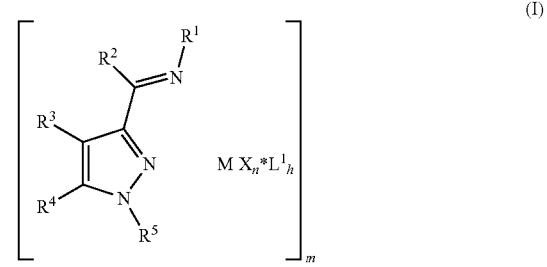

a process for preparing polyolefins by polymerization or copolymerization of at least one olefin in the presence of at least one olefin in the presence of at least one of the catalyst systems according to the invention and the use of the ligand systems according to the invention for preparing transition metal compounds.

5 Claims, No Drawings

OTHER PUBLICATIONS

James C. Randall, "A Review of High Resolution Liquid $^{13}$Carbon Nuclear Magnetic Resonance Characterizations of Ethylene-Based Polymers," *JMS-REV. Macromol. Chem. Phys.*, C29 (2 & 3), 201-317 (1989).

Gordon Dong et al., "The syntheses spectra and structures of five-coordinate cobalt (II) complexes of pyrazoly-containing ligands" *Inorganica Chimica ACTA*, 284(2), 266-272, CODEN: ICHAA3; ISSN: 0020-1693, 1999, XP002147959.

* cited by examiner

TRANSITION METAL COMPOUND, LIGAND SYSTEM, CATALYST SYSTEM AND PROCESS FOR PREPARING POLYOLEFINS

CROSS-REFERENCE TO RELATED APPLICATIONS

This application is the U.S. national stage under 35 U.S.C. §371 of International Application PCT/EP2006/011343, filed Nov. 27, 2006, claiming priority to German Patent Application No. 102005057559.5 filed Nov. 30, 2005, and provisional U.S. Appl. No. 60/753,272 filed Dec. 22, 2005; the disclosures of International Application PCT/EP2006/011343, German Patent Application 102005057559.5, and provisional U.S. Appl. No. 60/753,272, each as filed, are incorporated herein by reference.

The present invention relates to transition metal compounds of the formula (I)

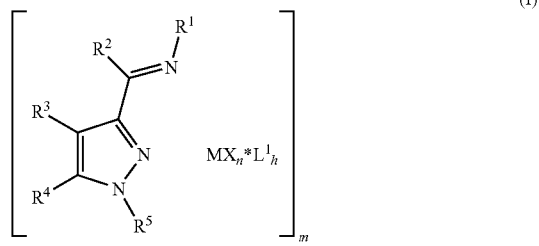

where
M is an element of group 3, 4, 5, 6, 7, 8, 9 or 10 of the Periodic Table of the Elements or the lanthanides,
the radicals X are identical or different and are each an organic or inorganic radical, with two radicals X also being able to be joined to one another to form a divalent radical,
n is 1, 2, 3 or 4,
$L^1$ is an organic or inorganic uncharged ligand,
h is an integer from 0 to 4,
$R^1$ is an organic radical having from 1 to 40 carbon atoms,
$R^2$ is hydrogen or an organic radical having from 1 to 40 carbon atoms,
or $R^1$ and $R^2$ together form a divalent organic group $T^1$ which has from 2 to 40 carbon atoms and together with the atoms connecting its ends forms a monocyclic or polycyclic ring system which may in turn be substituted and may comprise one or more further heteroatoms selected from the group consisting of the elements O, S, Se, Te, N, P and As in the ring system,
$R^3$ is hydrogen or an organic radical having from 1 to 40 carbon atoms,
$R^4$ is hydrogen or an organic radical having from 1 to 40 carbon atoms,
or $R^3$ and $R^4$ together form a divalent organic group $T^2$ which has from 2 to 40 carbon atoms and together with the atoms connecting its ends forms a monocyclic or polycyclic ring system which may in turn be substituted and may comprise one or more heteroatoms selected from the group consisting of the elements O, S, Se, Te, N, P and As in the ring system,
$R^5$ is an uncharged or negatively charged organic radical which has from 1 to 40 carbon atoms and may comprise a heteroatom selected from the group consisting of the elements N, O, P, S, As and Sb, and
m is an integer from 1 to 10.

In addition, the present invention relates to ligand systems having such a substitution pattern, catalyst systems comprising at least one of the transition metal compounds according to the invention, a process for preparing polyolefins by polymerization or copolymerization of at least one olefin in the presence of at least one of the catalyst systems according to the invention and the use of the ligand systems according to the invention for preparing transition metal compounds.

Research and development on the use of transition metal compounds, in particular metallocenes, as catalyst components for the polymerization and copolymerization of olefins with the objective of preparing tailored polyolefins has been carried out intensively in universities and in industry in the past 15 years.

Apart from metallocenes, new classes of transition metal compounds which comprise no cyclopentadienyl ligands are now being examined to an increasing extent as catalyst components. Examples are complexes of early transition metals comprising phenoxyimine ligands (EP 874 005) or complexes of "late transition metals" such as Ni, Pd (WO 96/23010), Fe or Co (WO 98127124) which comprise uncharged ligands such as diimines or bisiminopyridines. While Ni or Pd complexes (WO 96/23010) catalyze the formation of highly branched polymers which have hitherto been of little commercial interest, the use of Fe or Co complexes leads to formation of highly linear polyethylene having very small proportions of comonomer.

As G. J. P. Britovsek et al. show in Angew. Chem. Int. Ed. Engl. 1999, 38, 428, the search for highly versatile polymerization-active transition metal compounds continues to be of importance because of the great commercial importance of polyolefins. There is interest in finding polymerization-active transition metal compounds which have a particularly advantageous property profile from a process engineering point of view.

It was an object of the present invention to find new transition metal compounds which can be used as constituents of catalyst systems for the oligomerization, polymerization or copolymerization of ethylene.

We have accordingly found the transition metal compounds of the formula (I) mentioned at the outset.

M is an element of group 3, 4, 5, 6, 7, 8, 9 or 10 of the Periodic Table of the Elements or the lanthanides, for example scandium, yttrium, titanium, zirconium, hafnium, vanadium, niobium, tantalum, chromium, molybdenum, tungsten, manganese, iron, cobalt, nickel or palladium, preferably iron, cobalt or nickel, particularly preferably iron or cobalt, in particular iron.

The radicals X are identical or different, preferably identical, and are each an organic or inorganic radical, with two radicals X also being able to be joined to one another to form a divalent radical. In particular, X is halogen, for example fluorine, chlorine, bromine, iodine, preferably chlorine or bromine, hydrogen, $C_1$-$C_{20}$-, preferably $C_{1-4}$-alkyl, $C_2$-$C_{20}$-, preferably $C_2$-$C_4$-alkenyl, $C_6$-$C_{22}$-, preferably $C_6$-$C_{10}$-aryl, an alkylaryl or arylalkyl group having from 1 to 10, preferably from 1 to 4, carbon atoms in the alkyl radical and from 6 to 22, preferably from 6 to 10, carbon atoms in the aryl radical, —$OR^d$ or —$NR^dR^e$, preferably —$OR^d$, with two radicals X also being able to be joined to one another, preferably two radicals —$OR^d$, which are each, in particular, a substituted or unsubstituted 1,1'-bi-2-phenoxide radical. Two radicals X can also form a substituted or unsubstituted diene ligand, in particular a 1,3-diene ligand. The radicals $R^d$ and $R^e$ are each $C_1$-$C_{10}$-, preferably $C_1$-$C_4$-alkyl, $C_6$-$C_{15}$-, preferably $C_6$-$C_{10}$-aryl, alkylaryl, arylalkyl, fluoroalkyl or fluoroaryl each having from 1 to 10, preferably from 1 to 4, carbon atoms in the alkyl radical and from 6 to 22, preferably from 6 to 10, carbon atoms in the aryl radical. X is particularly preferably halogen, in particular chlorine or bromine.

n is 1, 2, 3 or 4 and usually corresponds to the oxidation number of M. n is preferably 2 or 3, in particular 2, when M is Fe or Co.

$L^1$ is an organic or inorganic uncharged ligand. Examples of such uncharged ligands are phosphanes such as triphenylphosphine, amines such as triethylamine or N,N,N',N'-tetramethylethylenediamine, ethers such as dialkyl ethers, e.g. diethyl ether, or cyclic ethers such as tetrahydrofuran, water, alcohols such as methanol or ethanol, pyridine, pyridine derivatives, for example 2-picoline, 3-picoline, 4-picoline, 2,3-lutidine, 2,4-lutidine, 2,5-lutidine, 2,6-lutidine or 3,5-lutidine, carbon monoxide and $C_1$-$C_{12}$-alkyl nitriles or $C_6$-$C_{14}$-aryl nitriles, e.g. acetonitrile, propionitrile, butyronitrile or benzonitrile. Singly or multiply ethylenically unsaturated double bond systems can also serve as ligand.

h is an integer from 0 to 4.

$R^1$ is an organic radical having from 1 to 40 carbon atoms, for example $C_1$-$C_{40}$-, preferably $C_1$-$C_{12}$-alkyl, $C_1$-$C_{10}$-, preferably $C_1$-$C_4$-fluoroalkyl, $C_2$-$C_{40}$-, preferably $C_2$-$C_{12}$-alkenyl, $C_6$-$C_{40}$-, preferably $C_6$-$C_{30}$-aryl, $C_6$-$C_{10}$-fluoroaryl, arylalkyl, arylalkenyl or alkylaryl each having from 1 to 10, preferably from 1 to 4, carbon atoms in the alkyl radical and from 6 to 22, preferably from 6 to 10, carbon atoms in the aryl radical, a saturated heterocycle having from 2 to 40, preferably from 3 to 30, carbon atoms or a $C_2$-$C_{40}$-, preferably $C_3$-$C_{30}$-heteroaromatic radical having in each case at least one heteroatom selected from the group consisting of the elements O, N, S, P and Se, in particular O, N and S, where the heteroaromatic radical may be substituted by further radicals $R^{16}$, where $R^{16}$ is an organic radical having from 1 to 20 carbon atoms, for example $C_1$-$C_{10}$-, preferably $C_1$-$C_4$-alkyl, $C_6$-$C_{15}$-, preferably $C_6$-$C_{10}$-aryl, alkylaryl, arylalkyl, fluoroalkyl or fluoroaryl each having from 1 to 10, preferably from 1 to 4, carbon atoms in the alkyl radical and from 6 to 18, preferably from 6 to 10, carbon atoms in the aryl radical, and a plurality of radicals $R^{16}$ can be identical or different.

$R^1$ is preferably $C_1$-$C_{12}$-alkyl, a substituted or unsubstituted $C_6$-$C_{40}$-, preferably $C_6$-$C_{30}$-aryl radical or $C_2$-$C_{40}$-, preferably $C_3$-$C_{30}$-heteroaromatic radical having at least one heteroatom selected from the group consisting of the elements O, N and S.

$R^1$ is particularly preferably a substituted or unsubstituted, preferably substituted, $C_6$-$C_{30}$-aryl radical such as 2-tolyl, 2,6-dimethylphenyl, 3,5-di(tert-butyl)phenyl, 2-chloro-4,6-dimethylphenyl, 2,6-diisopropylphenyl, 2-benzylphenyl, 2,6-dichlorophenyl or 2,6-dibromophenyl.

Very particular preference is given to $R^1$ being a phenyl radical which is substituted in at least the 2 and 6 positions (ortho, ortho' positions).

$R^2$ is hydrogen or an organic radical having from 1 to 40 carbon atoms, for example $C_1$-$C_{40}$-, preferably $C_1$-$C_{12}$-alkyl, $C_1$-$C_{10}$-, preferably $C_1$-$C_4$-fluoroalkyl, $C_2$-$C_{40}$-, preferably $C_2$-$C_{12}$-alkenyl, $C_6$-$C_{40}$-, preferably $C_6$-$C_{30}$-aryl, $C_6$-$C_{10}$-fluoroaryl, arylalkyl, arylalkenyl or alkylaryl each having from 1 to 10, preferably from 1 to 4, carbon atoms in the alkyl radical and from 6 to 22, preferably from 6 to 10, carbon atoms in the aryl radical, a saturated heterocycle having from 2 to 40, preferably from 3 to 30, carbon atoms or a $C_2$-$C_{40}$-, preferably $C_3$-$C_{30}$-heteroaromatic radical having in each case at least one heteroatom selected from the group consisting of the elements O, N, S, P and Se, in particular O, N and S, where the heteroaromatic radical may be substituted by further radicals $R^{16}$ as described above.

$R^2$ is preferably hydrogen, $C_1$-$C_{12}$-alkyl, a substituted or unsubstituted $C_6$-$C_{40}$-, preferably $C_6$-$C_{30}$-aryl radical or $C_2$-$C_{40}$-, preferably $C_3$-$C_{30}$-heteroaromatic radical having at least one heteroatom selected from the group consisting of the elements O, N and S.

$R^2$ is particularly preferably hydrogen.

The radicals $R^1$ and $R^2$ can together also form a divalent organic group $T^1$ which has from 2 to 40, in particular from 4 to 20, carbon atoms and together with the atoms connecting its ends forms a monocyclic or polycyclic ring system which may in turn be substituted and may comprise one or more further heteroatoms selected from the group consisting of the elements O, S, Se, Te, N, P and As, in particular O, S and N, in the ring system.

$R^3$ is hydrogen or an organic radical having from 1 to 40 carbon atoms, for example $C_1$-$C_{40}$-, preferably $C_1$-$C_{12}$-alkyl, $C_1$-$C_{10}$-, preferably $C_1$-$C_4$-fluoroalkyl, $C_2$-$C_{40}$-, preferably $C_2$-$C_{12}$-alkenyl, $C_6$-$C_{40}$-, preferably $C_6$-$C_{30}$-aryl, $C_6$-$C_{10}$-fluoroaryl, arylalkyl, arylalkenyl or alkylaryl each having from 1 to 10, preferably from 1 to 4, carbon atoms in the alkyl radical and from 6 to 22, preferably from 6 to 10, carbon atoms in the aryl radical, a saturated heterocycle having from 2 to 40, preferably from 3 to 30, carbon atoms or a $C_2$-$C_{40}$-, preferably $C_3$-$C_{30}$-heteroaromatic radical having at least one heteroatom selected from the group consisting of the elements O, N, S, P and Se, in particular O, N and S, where the heteroaromatic radical may be substituted by further radicals $R^{16}$ as described above.

$R^4$ is hydrogen or an organic radical having from 1 to 40 carbon atoms, for example $C_1$-$C_{40}$-, preferably $C_1$-$C_{12}$-alkyl, $C_1$-$C_{10}$-, preferably $C_1$-$C_4$-fluoroalkyl, $C_2$-$C_{40}$-, preferably $C_2$-$C_{12}$-alkenyl, $C_6$-$C_{40}$-, preferably $C_6$-$C_{30}$-aryl, $C_6$-$C_{10}$-fluoroaryl, arylalkyl, arylalkenyl or alkylaryl each having from 1 to 10, preferably from 1 to 4, carbon atoms in the alkyl radical and from 6 to 22, preferably from 6 to 10, carbon atoms in the aryl radical, a saturated heterocycle having from 2 to 40, preferably from 3 to 30, carbon atoms or a $C_2$-$C_{40}$-, preferably $C_3$-$C_{30}$-heteroaromatic radical having in each case at least one heteroatom selected from the group consisting of the elements O, N, S, P and Se, in particular O, N and S, where the heteroaromatic radical may be substituted by further radicals $R^{16}$ as described above.

The radicals $R^3$ and $R^4$ can also together form a divalent organic group $T^2$ which has from 2 to 40, in particular from 4 to 20, carbon atoms and together with the atoms connecting its ends forms a monocyclic or polycyclic ring system which may in turn be substituted and may comprise one or more heteroatoms selected from the group consisting of the elements O, S, Se, Te, N, P and As, in particular O, S and N, in the ring system.

Preference is given to the radicals $R^3$ and $R^4$ together forming a divalent organic group $T^2$

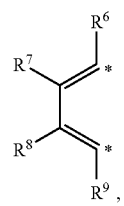

where the radicals $R^6$, $R^7$, $R^8$ and $R^9$ are identical or different and are each, independently of one another, hydrogen, halogen or an organic radical having from 1 to 40 carbon atoms, for example $C_1$-$C_{40}$-, preferably $C_1$-$C_{12}$-alkyl, $C_1$-$C_{10}$-, preferably $C_1$-$C_4$-fluoroalkyl, $C_2$-$C_{40}$-, preferably $C_2$-$C_{12}$-alkenyl, $C_6$-$C_{40}$-, preferably $C_6$-$C_{30}$-aryl, $C_6$-$C_{10}$-fluoroaryl, arylalkyl, arylalkenyl or alkylaryl each having from 1 to 10, preferably from 1 to 4, carbon atoms in the alkyl radical and from 6 to 22, preferably from 6 to 10, carbon atoms in the aryl radical, a saturated heterocycle having from 2 to 40, preferably from 3 to 30, carbon atoms or a $C_2$-$C_{40}$-, preferably $C_3$-$C_{30}$-heteroaromatic radical having in each case at least one heteroatom selected from the group consisting of the elements O, N, S, P and Se, in particular O, N and S, where the heteroaromatic radical may be substituted by further radicals $R^{16}$ as described above, or two adjacent radicals $R^6$, $R^7$, $R^8$ or $R^9$ together with the atoms connecting them form a monocyclic or polycyclic, substituted or unsubstituted ring system which has from 3 to 40, preferably from 5 to 30, carbon atoms and may also comprise heteroatoms selected from the group consisting of the elements Si, Ge, N, P, O, S, Se and Te, in particular O, S and N.

Particular preference is given to the radicals $R^6$, $R^7$, $R^8$ and $R^9$ each being hydrogen.

$R^5$ is an uncharged or negatively charged, preferably uncharged, organic radical which has from 1 to 40 carbon atoms and may comprise a heteroatom selected from the group consisting of the elements N, O, P, S, As and Sb, in particular N and O, preferably N.

$R^5$ is preferably an uncharged organic radical which has from 1 to 40 carbon atoms and comprises an sp²-hybridized nitrogen atom which has a double bond to a carbon atom.

$R^5$ is particularly preferably a radical

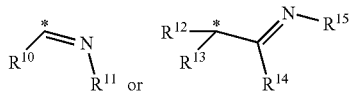

preferably

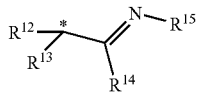

where $R^{10}$ is hydrogen or an organic radical having from 1 to 40 carbon atoms, preferably $C_1$-$C_{12}$-alkyl, a substituted or unsubstituted $C_6$-$C_{40}$-, preferably $C_6$-$C_{30}$-aryl radical or $C_2$-$C_{40}$-, preferably $C_3$-$C_{30}$-heteroaromatic radical having at least one heteroatom selected from the group consisting of the elements O, N and S, preferably a substituted or unsubstituted $C_6$-$C_{30}$-aryl radical, $R^{11}$ is an organic radical having from 1 to 40 carbon atoms, preferably $C_1$-$C_{12}$-alkyl, a substituted or unsubstituted $C_6$-$C_{40}$-, preferably $C_6$-$C_{30}$-aryl radical or $C_2$-$C_{40}$-, preferably $C_3$-$C_{30}$-heteroaromatic radical having at least one heteroatom selected from the group consisting of the elements O, N and S, preferably a substituted or unsubstituted $C_6$-$C_{30}$-aryl radical, or $R^{10}$ and $R^{11}$ together form a divalent organic group $T^3$ which has from 2 to 40, in particular from 3 to 30, carbon atoms and together with the atoms connecting its ends forms a monocyclic or polycyclic ring system which may in turn be substituted and may comprise one or more further heteroatoms selected from the group consisting of the elements O, N and S in the ring system, with preference being given to $R^{10}$ and $R^{11}$ together with the atoms connecting them forming a substituted or unsubstituted pyridine or quinoline radical, $R^{12}$ is hydrogen or an organic radical having from 1 to 40 carbon atoms, for example $C_1$-$C_{40}$-, preferably $C_1$-$C_{12}$-alkyl, $C_1$-$C_{10}$-, preferably $C_1$-$C_4$-fluoroalkyl, $C_2$-$C_{40}$-, preferably $C_2$-$C_{12}$-alkenyl, $C_6$-$C_{40}$-, preferably $C_6$-$C_{30}$-aryl, $C_6$-$C_{10}$-fluoroaryl, arylalkyl, arylalkenyl or alkylaryl each having from 1 to 10, preferably from 1 to 4, carbon atoms in the alkyl radical and from 6 to 22, preferably from 6 to 10 carbon atoms in the aryl radical, a saturated heterocycle having from 2 to 40, preferably from 3 to 30, carbon atoms or a $C_2$-$C_{40}$-, preferably $C_3$-$C_{30}$-heteroaromatic radical having in each case at least one heteroatom selected from the group consisting of the elements O, N, S, P and Se, in particular O, N and S, where the heteroaromatic radical may be substituted by further radicals $R^{16}$ as described above, preferably hydrogen, $R^{13}$ is hydrogen or an organic radical having from 1 to 40 carbon atoms, for example $C_1$-$C_{40}$-, preferably $C_1$-$C_{12}$-alkyl, $C_1$-$C_{10}$-, preferably $C_1$-$C_4$-fluoroalkyl, $C_2$-$C_{40}$-, preferably $C_2$-$C_{12}$-alkenyl, $C_6$-$C_{40}$-, preferably $C_6$-$C_{30}$-aryl, $C_6$-$C_{10}$-fluoroaryl, arylalkyl, arylalkenyl or alkylaryl each having from 1 to 10, preferably from 1 to 4, carbon atoms in the alkyl radical and from 6 to 22, preferably from 6 to 10 carbon atoms in the aryl radical, a saturated heterocycle having from 2 to 40, preferably from 3 to 30, carbon atoms or a $C_2$-$C_{40}$-, preferably $C_3$-$C_{30}$-heteroaromatic radical having in each case at least one heteroatom selected from the group consisting of the elements O, N, S, P and Se, in particular O, N and S, where the heteroaromatic radical may be substituted by further radicals $R^{16}$ as described above, preferably hydrogen, $R^{14}$ is hydrogen or an organic radical having from 1 to 40 carbon atoms, preferably $C_1$-$C_{12}$-alkyl, a substituted or unsubstituted $C_6$-$C_{40}$-, preferably $C_6$-$C_{30}$-aryl radical or $C_2$-$C_{40}$-, preferably $C_3$-$C_{30}$-heteroaromatic radical having at least one heteroatom selected from the group consisting of the elements O, N and S, $R^{15}$ is an organic radical having from 1 to 40 carbon atoms, preferably $C_1$-$C_{12}$-alkyl, a substituted or unsubstituted $C_6$-$C_{40}$-, preferably $C_6$-$C_{30}$-aryl radical or $C_2$-$C_{40}$-, preferably $C_3$-$C_{30}$-heteroaromatic radical having at least one heteroatom selected from the group consisting of the elements O, N and S, preferably a substituted or unsubstituted, preferably substituted, $C_6$-$C_{30}$-aryl radical which is, in particular, substituted in at least the 2 and 6 positions (ortho, ortho' positions), for example 2,6-dimethylphenyl, 2-chloro-4,6-dimethylphenyl, 2,6-diisopropylphenyl, 2,6-dichlorophenyl or 2,6-dibromophenyl, or $R^{14}$ and $R^{15}$ together form a divalent organic group $T^4$ which has from 2 to 40, preferably 3 to 30, carbon atoms and together with the atoms connecting its ends forms a monocyclic or polycyclic ring system which may in turn be substituted and may comprise one or more further heteroatoms selected from the group consisting of the elements O, N and S in the ring system, with preference being given to $R^{14}$ and $R^{15}$ together with the atoms connecting them forming a substituted or unsubstituted pyridine or quinoline radical.

m is an integer from 1 to 10.

The radicals $R^1$ to $R^{16}$ can, according to the invention, also comprise further heteroatoms, in particular heteroatoms selected from the group consisting of Si, N, P, O, S, F and Cl, or functional groups which may be capped by protective groups in place of carbon atoms or hydrogen atoms without altering the polymerization properties of the inventive transition metal compounds of the formula (I), as long as these heteroatoms or functional groups are chemically inert under the polymerization conditions.

Furthermore, the substituents according to the present invention are, unless restricted further, defined as follows:

The term "organic radical having from 1 to 40 carbon atoms" as used in the present context refers to, for example, $C_1$-$C_{40}$-alkyl radicals, $C_1$-$C_{10}$-fluoroalkyl radicals, $C_1$-$C_{12}$-alkoxy radicals, saturated $C_3$-$C_{20}$-heterocyclic radicals, $C_6$-$C_{40}$-aryl radicals, $C_2$-$C_{40}$-heteroaromatic radicals, $C_6$-$C_{10}$-fluoroaryl radicals, $C_6$-$C_{10}$-aryloxy radicals, $C_3$-$C_{18}$-trialkylsilyl radicals, $C_2$-$C_{20}$-alkenyl radicals, $C_2$-$C_{20}$-alkynyl radicals, $C_7$-$C_{40}$-arylalkyl radicals or $C_8$-$C_{40}$-arylalkenyl radicals. An organic radical is in each case derived from an organic compound. Thus, the organic compound methanol can in principle give rise to three organic radicals having 1 carbon atoms, namely methyl ($H_3C-$), methoxy ($H_3C-O-$) and hydroxymethyl ($HOC(H_2)-$).

The term "alkyl" as used in the present context encompasses linear or singly or multiply branched saturated hydrocarbons which may also be cyclic. Preference is given to $C_1$-$C_{18}$-alkyl such as methyl, ethyl, n-propyl, n-butyl, n-pentyl, n-hexyl, n-heptyl, n-octyl, n-nonyl, n-decyl, cyclopentyl, cyclohexyl, isopropyl, isobutyl, isopentyl, isohexyl, sec-butyl or tert-butyl.

The term "alkenyl" as used in the present context encompasses linear or singly or multiply branched hydrocarbons having one or more C—C double bond, which may be cumulated or alternating.

The term 'saturated heterocyclic radical' as used in the present context refers to, for example, monocyclic or polycyclic, substituted or unsubstituted hydrocarbon radicals in which one or more carbon atoms, CH groups and/or $CH_2$ groups are replaced by heteroatoms preferably selected from the group consisting of O, S, N and P. Preferred examples of substituted or unsubstituted saturated heterocyclic radicals are pyrrolidinyl, imidazolidinyl, pyrazolidinyl, piperidyl, piperazinyl, morpholinyl, tetrahydrofuranyl, tetrahydropyranyl, tetrahydrothiophenyl and the like, and also methyl-, ethyl-, propyl-, isopropyl- and tert-butyl-substituted derivatives thereof.

The term "aryl" as used in the present context refers to aromatic, optionally fused polyaromatic hydrocarbon substituents which may optionally be substituted by one or more linear or branched $C_1$-$C_{18}$-alkyl, $C_1$-$C_{18}$-alkoxy, $C_2$-$C_{10}$-alkenyl or $C_3$-$C_{15}$-alkylalkenyl groups. Preferred examples of substituted and unsubstituted aryl radicals are, in particular, phenyl, 4-methylphenyl, 4-ethylphenyl, 4-propylphenyl, 4-isopropylphenyl, 4-tert-butylphenyl, 4-methoxyphenyl, 1-naphthyl, 9-anthryl, 9-phenanthryl, 3,5-dimethylphenyl, 3,5-di-tert-butylphenyl or 4-trifluoromethylphenyl.

The term "heteroaromatic radical" as used in the present context refers to aromatic hydrocarbon substituents in which one or more carbon atoms are replaced by nitrogen, phosphorus, oxygen or sulfur atoms or combinations thereof. These can, like the aryl radicals, optionally be substituted by one or more linear or branched $C_1$-$C_{18}$-alkyl, $C_2$-$C_{10}$-alkenyl or $C_3$-$C_{15}$-alkylalkenyl groups. Preferred examples are furyl, thienyl, pyridyl, pyrazolyl, imidazolyl, oxazolyl, thiazolyl, pyrimidinyl, pyrazinyl and the like, and also methyl-, ethyl, propyl-, isopropyl- and tert-butyl-substituted derivatives thereof.

The term "arylalkyl" as used in the present context refers to aryl-comprising substituents whose alkyl radical is joined to the remainder of the molecule via an alkyl chain. Preferred examples are benzyl, substituted benzyl, phenethyl, substituted phenethyl and the like.

The terms fluoroalkyl and fluoroaryl mean that at least one hydrogen atom, preferably more than one hydrogen atom and a maximum of all hydrogen atoms of the corresponding substituent have been replaced by fluorine atoms. Examples of fluorine-comprising substituents which are preferred according to the invention are trifluoromethyl, 2,2,2-trifluoroethyl, pentafluorophenyl, 4-trifluoromethylphenyl, 4-perfluoro-tert-butylphenyl and the like.

Preference is given to transition metal compounds of the formula (I) as described above which have the formula (Ia)

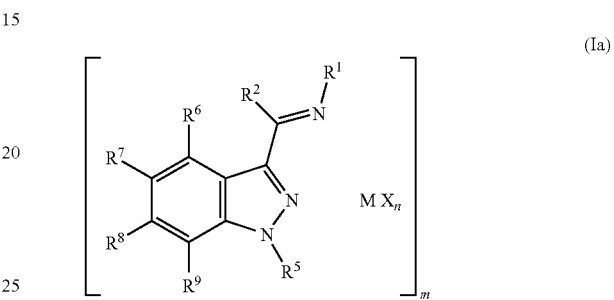

where

M is Fe, Co or Ni, preferably Fe or Co, in particular Fe,

X is halogen, such as fluorine, chlorine, bromine or iodine, in particular chlorine or bromine, n is 2, $R^1$ is $C_1$-$C_{12}$-alkyl, a substituted or unsubstituted $C_6$-$C_{40}$-aryl radical or $C_2$-$C_{40}$-heteroaromatic radical having at least one heteroatom selected from the group consisting of the elements O, N and S, $R^2$ is hydrogen, $C_1$-$C_{12}$-alkyl, a substituted or unsubstituted $C_6$-$C_{40}$-aryl radical or $C_2$-$C_{40}$-heteroaromatic radical having at least one heteroatom selected from the group consisting of the elements O, N and S, or $R^1$ and $R^2$ together form a divalent organic group $T_1$ which has from 3 to 30 carbon atoms and together with the atoms connecting its ends forms a monocyclic or polycyclic ring system which may in turn be substituted and may comprise one or more further heteroatoms selected from the group consisting of the elements O, N and S in the ring system, $R^6$, $R^7$, $R^8$ and $R^9$ are identical or different and are each, independently of one another, hydrogen, halogen or an organic radical having from 1 to 40 carbon atoms or two adjacent radicals $R^6$, $R^7$, $R^8$ or $R^9$ together with the atoms connecting them form a monocyclic or polycyclic, substituted or unsubstituted ring system which has from 3 to 40 carbon atoms and may also comprise heteroatoms selected from the group consisting of the elements Si, Ge, N, P, O, S, Se and Te, $R^5$ is a rdical

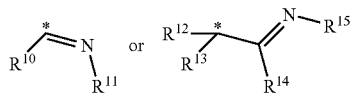

preferably

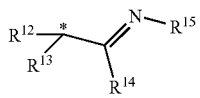

where
$R^{10}$ is hydrogen, $C_1$-$C_{12}$-alkyl, a substituted or unsubstituted $C_6$-$C_{40}$-aryl radical or $C_2$-$C_{40}$-heteroaromatic radical having at least one heteroatom selected from the group consisting of the elements O, N and S,
$R^{11}$ is $C_1$-$C_{12}$-alkyl, a substituted or unsubstituted $C_6$-$C_{40}$-aryl radical or $C_2$-$C_{40}$-heteroaromatic radical having at least one heteroatom selected from the group consisting of the elements O, N and S, or $R^{10}$ and $R^{11}$ together form a divalent organic group $T^3$ which has from 3 to 30 carbon atoms and together with the atoms connecting its ends forms a monocyclic or polycyclic ring system which may in turn be substituted and may comprise one or more further heteroatoms selected from the group consisting of the elements O, N and S in the ring system,
$R^{12}$ is hydrogen or an organic radical having from 1 to 40 carbon atoms,
$R^{13}$ is hydrogen or an organic radical having from 1 to 40 carbon atoms,
$R^{14}$ is hydrogen, $C_1$-$C_{12}$-alkyl, a substituted or unsubstituted $C_6$-$C_{40}$-aryl radical or $C_2$-$C_{40}$-heteroaromatic radical having at least one heteroatom selected from the group consisting of the elements O, N and S.
$R^{15}$ is $C_1$-$C_{12}$-alkyl, a substituted or unsubstituted $C_6$-$C_{40}$-aryl radical or $C_2$-$C_{40}$-heteroaromatic radical having at least one heteroatom selected from the group consisting of the elements O, N and S, or $R^{14}$ and $R^{15}$ together form a divalent organic group $T^4$ which has from 3 to 30 carbon atoms and together with the atoms connecting its ends forms a monocyclic or polycyclic ring system which may in turn be substituted and may comprise one or more further heteroatoms selected from the group consisting of the elements O, N and S in the ring system, and m is an integer from 1 to 4.

$R^1$ is $C_1$-$C_{12}$-alkyl, a substituted or unsubstituted $C_6$-$C_{40}$-, preferably $C_6$-$C_{30}$-aryl radical or $C_2$-$C_{40}$-, preferably $C_3$-$C_{30}$-heteroaromatic radical having at least one heteroatom selected from the group consisting of the elements O, N and S. $R^1$ is preferably a substituted or unsubstituted, preferably substituted, $C_6$-$C_{30}$-aryl radical, for example 2-tolyl, 2,6-dimethylphenyl, 3,5-di-tert-butyl)phenyl, 2-chloro-4,6-dimethylphenyl, 2,6-diisopropylphenyl, 2-benzylphenyl, 2,6-dichlorophenyl or 2,6-dibromophenyl. $R^1$ is particularly preferably a phenyl radical which is substituted in at least the 2 and 6 positions (ortho, ortho' positions).

$R^2$ is hydrogen, $C_1$-$C_{12}$-alkyl, a substituted or unsubstituted $C_6$-$C_{40}$-, preferably $C_6$-$C_{30}$-aryl radical or $C_2$-$C_{40}$-, preferably $C_3$-$C_{30}$-heteroaromatic radical having at least one heteroatom selected from the group consisting of the elements O, N and S. $R^2$ is preferably hydrogen.

The radicals $R^1$ and $R^2$ can together also form a divalent organic group $T^1$ which has from 3 to 30, in particular from 4 to 20, carbon atoms and together with the atoms connecting its ends forms a monocyclic or polycyclic ring system which may in turn be substituted and may comprise one or more further heteroatoms selected from the group consisting of the elements O, N and S in the ring system.

The radicals $R^6$, $R^7$, $R^8$ and $R^9$ are identical or different and are each, independently of one another, hydrogen, halogen such as fluorine, chlorine, bromine or iodine, in particular fluorine or chlorine, or an organic radical having from 1 to 40 carbon atoms, for example $C_1$-$C_{40}$-, preferably $C_1$-$C_{10}$-alkyl, $C_1$-$C_{10}$-, preferably $C_1$-$C_4$-fluoroalkyl, $C_2$-$C_{40}$-, preferably $C_2$-$C_8$-alkenyl, $C_6$-$C_{40}$-, preferably $C_6$-$C_{10}$-aryl, $C_6$-$C_{10}$-fluoroaryl, arylalkyl, arylalkenyl or alkylaryl each having from 1 to 10, preferably from 1 to 4, carbon atoms in the alkyl radical and from 6 to 22, preferably from 6 to 10, carbon atoms in the aryl radical, a saturated heterocycle having from 2 to 40, preferably from 3 to 30, carbon atoms or a $C_2$-$C_{40}$-, preferably $C_3$-$C_{30}$-heteroaromatic radical having in each case at least one heteroatom selected from the group consisting of the elements O, N, S, P and Se, in particular O, N and S, where the heteroaromatic radical may be substituted by further radicals $R^{16}$ as described above, or two adjacent radicals $R^6$, $R^7$, $R^8$ or $R^9$ together with the atoms connecting them form a monocyclic or polycyclic, substituted or unsubstituted ring system which has from 3 to 40, preferably from 5 to 30, carbon atoms and may also comprise heteroatoms selected from the group consisting of the elements Si, Ge, N, P, O, S, Se and Te, preferably N, O or S, $R^{10}$ is hydrogen, $C_1$-$C_{12}$-alkyl, a substituted or unsubstituted $C_6$-$C_{40}$-, preferably $C_6$-$C_{30}$-aryl radical or $C_2$-$C_{40}$-, preferably $C_3$-$C_{30}$-heteroaromatic radical having at least one heteroatom selected from the group consisting of the elements O, N and S. $R^{10}$ is preferably a substituted or unsubstituted $C_6$-$C_{40}$-aryl radical.

$R^{11}$ is $C_1$-$C_{12}$-alkyl, a substituted or unsubstituted $C_8$-$C_{40}$-, preferably $C_6$-$C_{30}$-aryl radical or $C_2$-$C_{40}$-, preferably $C_3$-$C_{30}$-heteroaromatic radical having at least one heteroatom selected from the group consisting of the elements O, N and S. $R^{11}$ is preferably a substituted or unsubstituted $C_6$-$C_{40}$-aryl radical.

The radicals $R^{10}$ and $R^{11}$ can together also form a divalent organic group $T^3$ which has from 3 to 30 carbon atoms and together with the atoms connecting its ends forms a monocyclic or polycyclic ring system which may in turn be substituted and may comprise one or more further heteroatoms selected from the group consisting of the elements O, N and S in the ring system.

$R^{12}$ is hydrogen or an organic radical having from 1 to 40 carbon atoms, for example $C_1$-$C_{40}$-, preferably $C_1$-$C_{10}$-alkyl, $C_1$-$C_{10}$-, preferably $C_1$-$C_4$-fluoroalkyl, $C_2$-$C_{40}$-, preferably $C_2$-$C_8$-alkenyl, $C_6$-$C_{40}$-, preferably $C_6$-$C_{18}$-aryl, $C_6$-$C_{10}$-fluoroaryl, arylalkyl, arylalkenyl or alkylaryl each having from 1 to 10, preferably 1 to 4, carbon atoms in the alkyl radical and from 6 to 22, preferably from 6 to 10, carbon atoms in the aryl radical, a saturated heterocycle having from 2 to 40, preferably from 3 to 30, carbon atoms or a $C_2$-$C_{40}$-, preferably $C_3$-$C_{30}$-heteroaromatic radical having in each case at least one heteroatom selected from the group consisting of the elements O, N, S, P and Se, in particular O, N and S, where the heteroaromatic radical may be substituted by further radicals $R^{16}$ as described above. $R^{12}$ is preferably hydrogen.

$R^{13}$ is hydrogen or an organic radical having from 1 to 40 carbon atoms, for example $C_1$-$C_{40}$-, preferably $C_1$-$C_{10}$-alkyl, $C_1$-$C_{10}$-, preferably $C_1$-$C_4$-fluoroalkyl, $C_2$-$C_{40}$-, preferably $C_2$-$C_8$-alkenyl, $C_6$-$C_{40}$-, preferably $C_6$-$C_{18}$-aryl, $C_6$-$C_{10}$-fluoroaryl, arylalkyl, arylalkenyl or alkylaryl each having from 1 to 10, preferably 1 to 4, carbon atoms in the alkyl radical and from 6 to 22, preferably from 6 to 10, carbon atoms in the aryl radical, a saturated heterocycle having from 2 to 40, preferably from 3 to 30, carbon atoms or a $C_2$-$C_{40}$-, preferably $C_3$-$C_{30}$-heteroaromatic radical having in each case at least one heteroatom selected from the group consisting of the elements O, N, S, P and Se, in particular O, N and S, where the heteroaromatic radical may be substituted by further radicals $R^{16}$ as described above. $R^{13}$ is preferably hydrogen.

$R^{14}$ is hydrogen, $C_1$-$C_{12}$-alkyl, a substituted or unsubstituted $C_6$-$C_{40}$-, preferably $C_8$-$C_{30}$-aryl radical or $C_2$-$C_{40}$-, preferably $C_3$-$C_{30}$-heteroaromatic radical having at least one heteroatom selected from the group consisting of the elements O, N and S.

$R^{15}$ is $C_1$-$C_{12}$-alkyl, a substituted or unsubstituted $C_6$-$C_{40}$-, preferably $C_6$-$C_{30}$-aryl radical or $C_2$-$C_{40}$-, preferably $C_3$-$C_{30}$-heteroaromatic radical having at least one heteroatom selected from the group consisting of the elements O, N and S. $R^{15}$ is preferably a substituted or unsubstituted, preferably substituted $C_6$-$C_{30}$-aryl radical which is, in particular, substituted in at least the 2 and 6 positions (ortho, ortho' positions), for example 2,6-dimethylphenyl, 2-chloro-4,6-dimethylphenyl, 2,6-diisopropylphenyl, 2,6-dichlorophenyl or 2,6-dibromophenyl.

The radicals $R^{14}$ and $R^{15}$ can together also form a divalent organic group $T^4$ which has from 3 to 30 carbon atoms and together with the atoms connecting its ends forms a monocyclic or polycyclic ring system which may in turn be substituted and may comprise one or more further heteroatoms selected from the group consisting of the elements O, N and S in the ring system.

m is an integer from 1 to 4, preferably 1 or 2.

Illustrative examples of the inventive transition metal compounds of the formula (I) or (Ia), which do not, however, restrict the invention, are:

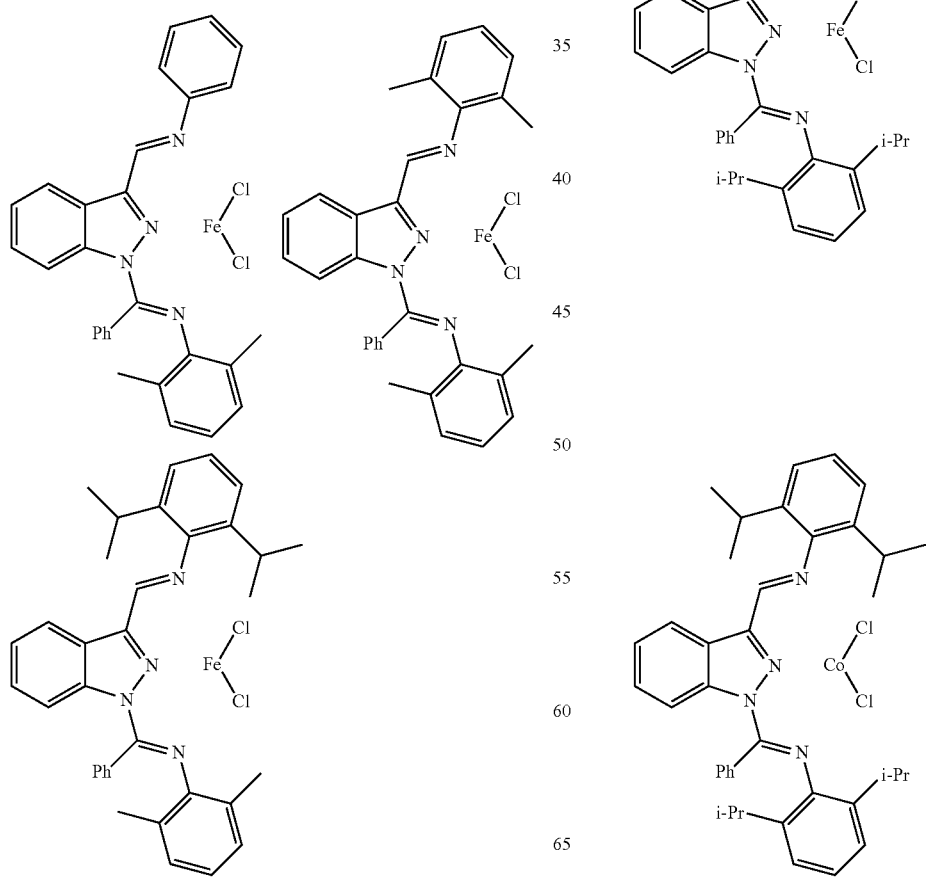

-continued

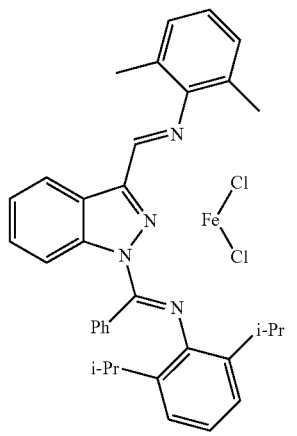

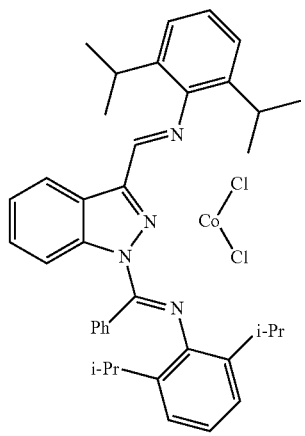

-continued
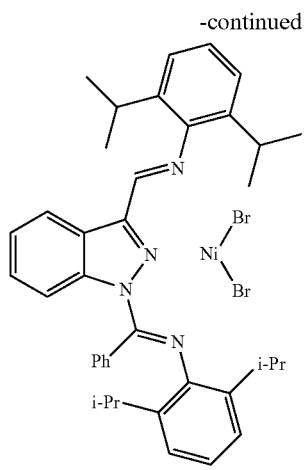
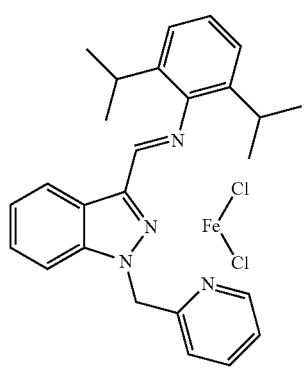
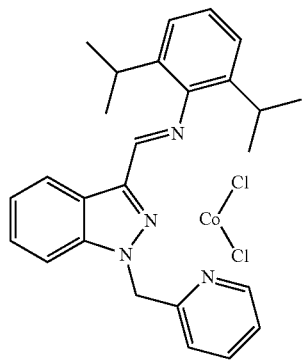
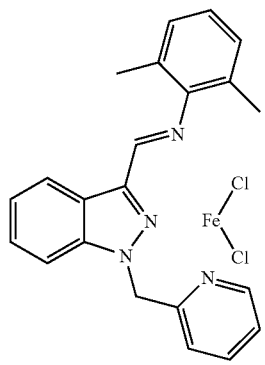
-continued
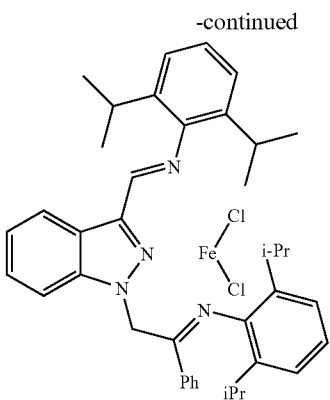
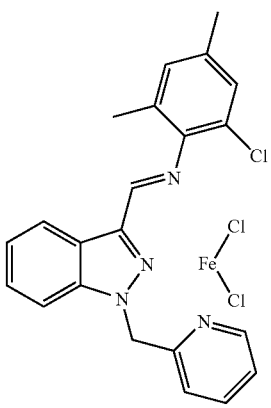
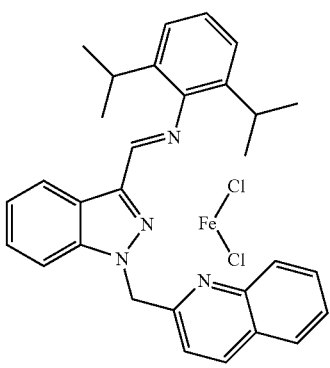
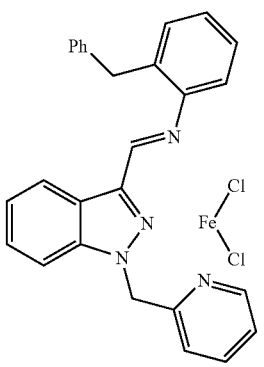

-continued

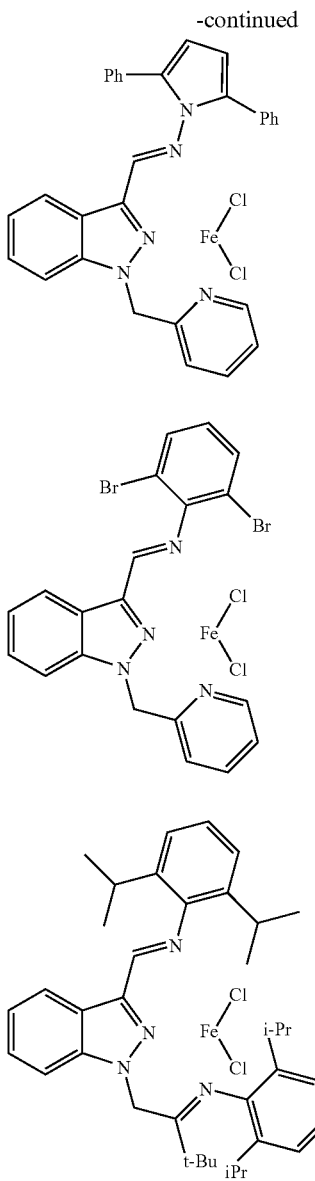

The inventive transition metal compounds of the formula (I) or (Ia) can be prepared by methods as described in the examples.

The invention further provides a ligand system of the formula (II)

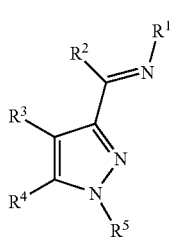
(II)

where $R^1$, $R^2$, $R^3$, $R^4$ and $R^5$ are as defined in the formula (I).

Preference is given to a ligand system of the formula (IIa)

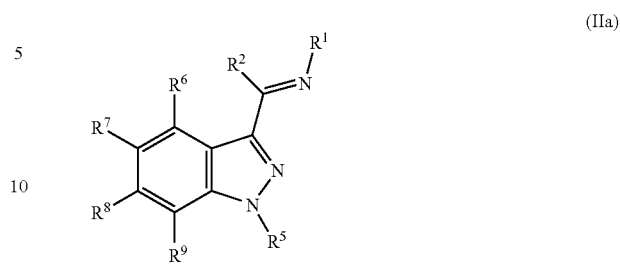
(IIa)

where the variables $R^1$, $R^2$, $R^5$, $R^6$, $R^7$, $R^8$ and $R^9$ are as defined in the formula (Ia).

The substitution pattern of the ligand systems of the formula (II) or (IIa) is critical for the particular polymerization properties of the transition metal compounds comprising these ligand systems.

The ligand systems of the formula (II) or (IIa) can be prepared as described in the examples.

The invention further provides transition metal compounds which are obtainable by reacting a ligand system of the formula (II) or (IIa) with a transition metal starting compound $$MX_n * L^1_h$$

where the variables and indices M, X, n, $L^1$ and h are as defined in the formula (I).

The invention likewise provides for the use of a ligand system of the formula (II) or (IIa) for preparing a transition metal compound, preferably for preparing a transition metal compound having an element selected from the group of elements consisting of Fe, Co and Ni, preferably Fe and Co, in particular Fe.

Thus, a process for preparing a transition metal compound comprising a ligand system of the formula (II) or (IIa), which comprises reacting a ligand system of the formula (II) or (IIa) with a starting compound comprising a transition metal, is also subject matter of the present invention. A further possible way of preparing the transition metal compounds of the formula (I) or (Ia) comprises synthesizing the ligand from suitable ligand building blocks in the presence of a starting compound comprising a transition metal in the sense of a template-controlled synthesis. The principle of this one-pot synthesis is described, for example, in WO 2000/008034.

The transition metal compounds of the invention are, particularly in the presence of suitable cocatalysts, a highly active catalyst constituent for the polymerization of olefins, in particular for the polymerization of ethene.

The cocatalyst which together with the transition metal compound of the invention forms a polymerization-active catalyst system is able to convert the transition metal compound into a species which displays polymerization activity toward at least one olefin. The catalyst is therefore sometimes also referred to as activating compound. The polymerization-active transition metal species is frequently a cationic species. In this case, the cocatalyst is also frequently referred to as cation-forming compound.

The present invention therefore further provides a catalyst system for the polymerization of olefins, in particular ethylene, comprising at least one transition metal compound according to the invention and at least one cocatalyst which is able to convert the transition metal compound into a species which displays polymerization activity toward at least one olefin.

Suitable cocatalysts or cation-forming compounds are, for example, compounds such as an aluminoxane, a strong uncharged Lewis acid, an ionic compound having a Lewis-acid cation or an organic compound having a Brönsted acid as cation. Preference is given to using an aluminoxane as cocatalyst.

To prepare such a catalyst system, the transition metal compound according to the invention is preferably preactivated by means of an aluminoxane before use in the polymerization reaction. In this preactivation step, the transition metal compound, preferably as such or as a solution, is brought into contact with an aluminoxane, in particular a solution of methylaluminoxane, for a particular time, e.g. from 1 minute to 48 hours, preferably from 5 minutes to 4 hours, in order to form the catalyst system.

As aluminoxanes, it is possible to use, for example, the compounds described in WO 00/31090. Particularly useful aluminoxanes are open-chain or cyclic aluminoxane compounds of the general formula (XI) or (XII)

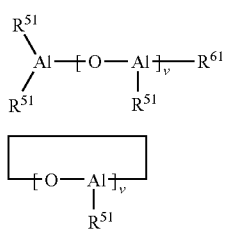

where $R^{51}$ is a $C_1$-$C_4$-alkyl group, preferably a methyl or ethyl group, and v is an integer from 5 to 30, preferably from 10 to 25.

These oligomeric aluminoxane compounds are usually prepared by reacting a solution of trialkylaluminum with water. In general, the oligomeric aluminoxane compounds obtained in this way are in the form of mixtures of both linear and cyclic chain molecules of various lengths, so that v is to be regarded as a mean. The aluminoxane compounds can also be present in admixture with other metal alkyls, preferably aluminum alkyls.

Furthermore, modified aluminoxanes in which some of the hydrocarbon radicals or hydrogen atoms have been replaced by alkoxy, aryloxy, siloxy or amide radicals can also be used in place of the aluminoxane compounds of the general formula (XI) or (XII).

It has been found to be advantageous to use the transition metal compound according to the invention and the aluminoxane compounds in such amounts that the atomic ratio of aluminum from the aluminoxane compounds to the transition metal from the transition metal compound is in the range from 1:1 to 100 000:1, preferably in the range from 5:1 to 20 000:1 and in particular in the range from 10:1 to 2000:1.

As strong, uncharged Lewis acids, preference is given to compounds of the general formula (XIII)

$$M^3X^1X^2X^3 \qquad (XIII)$$

where $M^3$ is an element of group 13 of the Periodic Table of the Elements, in particular B, Al or Ga, preferably B, $X^1$, $X^2$ and $X^3$ are each, independently of one another, hydrogen, $C_1$-$C_{10}$-alkyl, $C_6$-$C_{15}$-aryl, alkylaryl, arylalkyl, haloalkyl or haloaryl each having from 1 to 10 carbon atoms in the alkyl radical and from 6 to 20 carbon atoms in the aryl radical or fluorine, chlorine, bromine or iodine, in particular haloaryl, preferably pentafluorophenyl.

Further examples of strong, uncharged Lewis acids are given in WO 00/31090.

Particular preference is given to compounds of the general formula (XIII) in which $X^1$, $X^2$ and $X^3$ are identical, preferably tris(pentafluorophenyl)borane.

Strong uncharged Lewis acids suitable as cocatalyst or cation-forming compounds also include the reaction products of a boronic acid with two equivalents of a trialkylaluminum or the reaction products of a trialkylaluminum with two equivalents of an acidic fluorinated, in particular perfluorinated, carbon compound such as pentafluorophenol or bis (pentafluorophenyl)borinic acid.

Suitable ionic compounds having Lewis-acid cations are salt-like compounds of the cation of the general formula (XIV)

$$[(Y^{a+})Q^1Q^2\ldots Q^z]^{d+} \qquad (XIV)$$

where

Y is an element of groups 1 to 16 of the Periodic Table of the Elements, $Q^1$ to $Q^z$ are singly negatively charged groups such as $C_1$-$C_{28}$-alkyl, $C_6$-$C_{15}$-aryl, alkylaryl, arylalkyl, haloalkyl, haloaryl each having from 6 to 20 carbon atoms in the aryl radical and from 1 to 28 carbon atoms in the alkyl radical, $C_3$-$C_{10}$-cycloalkyl which may optionally bear $C_1$-$C_{10}$-alkyl groups as substituents, halogen, $C_1$-$C_{28}$-alkoxy, $C_8$-$C_{15}$-aryloxy, silyl or mercaptyl groups, a is an integer from 1 to 6 and z is an integer from 0 to 5, and d corresponds to the difference a–z, but d is greater than or equal to 1.

Particularly useful cations are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are also mentioned in WO 91/09882, preferably tetrakis(pentafluorophenyl)borate.

Salts having noncoordinating anions can also be prepared by combining a boron or aluminum compound, e.g. an aluminum alkyl, with a second compound which can react to link two or more boron or aluminum atoms, e.g. water, and a third compound which forms an ionizing ionic compound with the boron or aluminum compound, e.g. triphenylchloromethane. In addition, a fourth compound which likewise reacts with the boron or aluminum compound, e.g. pentafluorophenol, can be added.

Ionic compounds having Brönsted acids as cations preferably likewise have noncoordinating counterions. As Brönsted acid, particular preference is given to protonated amine or aniline derivatives. Preferred cations are N,N-dimethylanilinium, N,N-dimethylcylohexylammonium and N,N-dimethylbenzylammonium and also derivatives of the latter two.

Ionic compounds preferred as cocatalysts or cation-forming compounds are, in particular, N,N-dimethylanilinium tetrakis(pentafluorophenyl)borate, N,N-dimethylcyclohexylammonium tetrakis(pentafluorophenyl)borate or N,N-dimethylbenzylammonium tetrakis(pentafluorophenyl) borate.

It is also possible for two or more borate anions to be joined to one another, as in the dianion [$(C_6F_5)_2B$—$C_6F_4$—B $(C_6F_6)_2]^{2-}$, or the borate anion can be bound via a bridge having a suitable functional group to the surface of a support particle.

Further suitable cocatalysts or cation-forming compounds are listed in WO 00/31090.

The amount of strong, uncharged Lewis acids, ionic compounds having Lewis-acid cations or ionic compounds having Brönsted acids as cations is usually from 0.1 to 20 equivalents, preferably from 1 to 10 equivalents, based on the transition metal compound according to the invention, in the process of the invention.

Suitable cocatalysts or cation-forming compounds also include boron-aluminum compounds such as di[bis(pentafluorophenyl)boroxy]methylalane. Examples of such boron-aluminum compounds are disclosed in WO 99/06414.

It is also possible to use mixtures of all the abovementioned cocatalysts or cation-forming compounds. Preferred mixtures comprise aluminoxanes, in particular methylaluminoxane, and an ionic compound, in particular one comprising the tetrakis(pentafluorophenyl)borate anion, and/or a strong uncharged Lewis acid, in particular tris(pentafluorophenyl)borane.

Both the transition metal compound of the invention and the cocatalysts or cation-forming compounds are preferably used in a solvent, preferably an aromatic hydrocarbon having from 6 to 20 carbon atoms, in particular xylenes and toluene.

The catalyst can further comprise a metal compound of the general formula (XV), $$M^4(R^{52})_r(R^{53})_s(R^{54})_t \quad (XV)$$

where $M^4$ is an alkali metal, an alkaline earth metal or a metal of group 13 of the Periodic Table, i.e. boron, aluminum, gallium, indium or thallium, $R^{52}$ is hydrogen, $C_1$-$C_{10}$-alkyl, $C_6$-$C_{15}$-aryl, alkylaryl or arylalkyl each having from 1 to 10 carbon atoms in the alkyl radical and from 6 to 20 carbon atoms in the aryl radical, $R^{53}$ and $R^{54}$ are identical or different and are each hydrogen, halogen, $C_1$-$C_{10}$alkyl, $C_6$-$C_{15}$-aryl, alkylaryl, arylalkyl or alkoxy each having from 1 to 10 carbon atoms in the alkyl radical and from 6 to 20 carbon atoms in the aryl radical, r is an integer from 1 to 3, and s and t are integers from 0 to 2, with the sum r+s+t corresponding to the valence of $M^4$, where the metal compound of the formula (XV) is usually not identical to the cocatalyst or the cation-forming compound. It is also possible to use mixtures of various metal compounds of the formula (XV).

Among the metal compounds of the general formula (XV), preference is given to those in which $M^4$ is lithium, magnesium or aluminum and $R^{53}$ and $R^{54}$ are each $C_1$-$C_{10}$-alkyl.

Particularly preferred metal compounds of the formula (XV) are n-butyllithium, n-butyl-n-octylmagnesium, n-butyl-n-heptylmagnesium, tri-n-hexylaluminum, triisobutylaluminum, triethylaluminum and trimethylaluminum and mixtures thereof.

When a metal compound of the formula (XV) is used, it is preferably present in the catalyst in such an amount that the molar ratio of $M^4$ from formula (XV) to the transition metal atom from the transition metal compound according to the invention is from 800:1 to 1:1, in particular from 200:1 to 2:1.

Preference is given to a catalyst system which comprises a support in addition to a transition metal compound according to the invention and at least one cocatalyst.

To obtain such a supported catalyst system, the unsupported catalyst system can be reacted with a support. The order in which the support, the transition metal compound according to the invention and the cocatalyst are combined is in principle immaterial. The transition metal compounds according to the invention and the cocatalyst can be immobilized independently of one another or simultaneously. After the individual process steps, the solid can be washed with suitably inert solvents, e.g. aliphatic or aromatic hydrocarbons.

As support, preference is given to using finely divided supports which can be any organic or inorganic, inert solid. In particular, the support can be a porous solid such as talc, a sheet silicate, an inorganic oxide or a finely divided polymer powder (e.g. polyolefin).

Suitable inorganic oxides may be found among the oxides of elements of groups 2, 3, 4, 5, 13, 14, and 16 of the Periodic Table of the Elements. Examples of oxides preferred as supports comprise silicon dioxide, aluminum oxide and mixed oxides of the elements calcium, aluminum, silicon, magnesium or titanium and also corresponding oxide mixtures. Other inorganic oxides which can be used either alone or in combination with the abovementioned preferred oxidic supports are, for example, MgO, $ZrO_2$, $TiO_2$ or $B_2O_3$. A preferred mixed oxide is, for example, calcined hydrotalcite.

The support materials used preferably have a specific surface area in the range from 10 to 1000 $m^2/g$, a pore volume in the range from 0.1 to 5 ml/g and a mean particle size of from 1 to 500 μm. Preference is given to supports having a specific surface area in the range from 50 to 500 $m^2/g$, a pore volume in the range from 0.5 to 3.5 ml/g and a mean particle size in the range from 5 to 350 μm. Particular preference is given to supports having a specific surface area in the range from 200 to 400 $m^2/g$, a pore volume in the range from 0.8 to 3.0 ml/g and a mean particle size of from 10 to 100 μm.

The inorganic support can be subjected to a thermal treatment, e.g. to remove adsorbed water. Such a drying treatment is generally carried out at temperatures in the range from 80 to 300° C., preferably from 100 to 200° C., with drying at from 100 to 200° C. preferably being carried out under reduced pressure and/or under a blanket of inert gas (e.g. nitrogen), or the inorganic supports can be calcined at temperatures of from 200 to 1000° C. to produce the desired structure of the solid and/or set the desired OH concentration on the surface. The support can also be treated chemically using customary desiccants such as metal alkyls, preferably aluminum alkyls, chlorosilanes or $SiCl_4$, or else methylaluminoxane. Appropriate treatment methods are described, for example, in WO 00/31090.

The inorganic support material can also be chemically modified. For example, treatment of silica gel with $(NH_4)_2SiF_6$ leads to fluorination of the silica gel surface, or treatment of silica gels with silanes comprising nitrogen-, fluorine- or sulfur-comprising groups leads to correspondingly modified silica gel surfaces.

Organic support materials such as finely divided polyolefin powders (e.g. polyethylene, polypropylene or polystyrene) can also be used and should preferably likewise be freed of adhering moisture, solvent residues or other impurities by means of appropriate purification and drying operations before use. It is also possible to use functionalized polymer supports, e.g. ones based on polystyrenes, via whose functional groups, for example ammonium or hydroxy groups, at least one of the catalyst components can be immobilized.

In a preferred embodiment of the preparation of the supported catalyst system, at least one of the transition metal compounds according to the invention is brought into contact with at least one cocatalyst as activating or cation-forming compound in a suitable solvent, giving a soluble or insoluble, preferably soluble, reaction product, an adduct or a mixture.

The preparation obtained in this way is then mixed with the dehydrated or passivated support material, the solvent is removed and the resulting supported transition metal catalyst system is dried to ensure that all or most of the solvent is removed from the pores of the support material. The supported catalyst is usually obtained as a free-flowing powder. Examples of the industrial implementation of the above process are described in WO 96/00243, WO 98/40419 or WO 00/05277.

In a further preferred embodiment, the cocatalyst or the cation-forming compound is firstly applied to the support component and this supported cocatalyst or this cation-forming compound is subsequently brought into contact with the transition metal coordination compound.

Further useful catalyst systems are therefore combinations obtained by combining the following components:

1st component: at least one defined boron or aluminum compound,

2nd component: at least one uncharged compound which has at least one acidic hydrogen atom, 3rd component at least one support, preferably an inorganic oxidic support, and optionally as 4th component a base, preferably an organic nitrogen-comprising base, for example an amine, an aniline derivative or a nitrogen heterocycle.

The boron or aluminum compounds used in the preparation of the supported cocatalysts are preferably compounds of the formula (XVI)

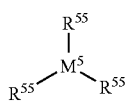

(XVI)

where the radicals $R^{55}$ are identical or different and are each hydrogen, halogen, $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalky, $C_7$-$C_{40}$-haloarylalkyl, $C_7$-$C_{40}$-alkylaryl, $C_7$-$C_{40}$-haloalkylaryl or an OSi$R^{56}_3$ group, where the radicals $R^{56}$ are identical or different and are each hydrogen, halogen, $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl, $C_7$-$C_{40}$-haloalkylaryl, preferably hydrogen, $C_1$-$C_8$-alkyl or $C_7$-$C_{20}$-arylalkyl, and $M^5$ is boron or aluminum, preferably aluminum.

Particularly preferred compounds of the formula (XVI) are trimethylaluminum, triethylaluminum and triisobutylaluminum.

The uncharged compounds which have at least one acidic hydrogen atom and can react with compounds of the formula (XVI) are preferably of the formula (XVII), (XVIII) or (XIX),

where the radicals $R^{57}$ are identical or different and are each hydrogen, halogen, a boron-free organic radical having from 1 to 40 carbon atoms, e.g. $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalky, $C_7$-$C_{40}$-haloarylalky, $C_7$-$C_{40}$-alkylaryl, $C_7$-$C_{40}$-haloalkylaryl, an Si($R^{59}$)$_3$ radical or a CH(Si$R^{59}_3$)$_2$ radical, where $R^{59}$ is a boron-free organic radical having from 1 to 40 carbon atoms, e.g. $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalky, $C_7$-$C_{40}$-haloarylalky, $C_7$-$C_{40}$-alkylaryl, $C_7$-$C_{40}$-haloalkylaryl, and $R^{58}$ is a divalent organic group having from 1 to 40 carbon atoms, e.g. $C_1$-$C_{20}$-alkylene, $C_1$-$C_{20}$-haloalkylene, $C_6$-$C_{20}$-arylene, $C_6$-$C_{20}$-haloarylene, $C_7$-$C_{40}$-arylalkylene, $C_7$-$C_{40}$-haloarylalkylene, $C_7$-$C_{40}$-alkylarylene, $C_7$-$C_{40}$-haloalkylarylene, D is an element of group 16 of the Periodic Table of the Elements or an N$R^{60}$ group, where $R^{60}$ is hydrogen or a $C_1$-$C_{20}$-hydrocarbon radical such as $C_1$-$C_{20}$-alkyl or $C_6$-$C_{20}$-aryl, with preference being given to D being oxygen, and h is 1 or 2.

Suitable compounds of the formula (XVII) are water, alcohols, phenol derivatives, thiophenol derivatives or aniline derivatives, with halogenated and in particular perfluorinated alcohols and phenols being of particular importance. Examples of particularly useful compounds are pentafluorophenol, 1,1-bis(pentafluorophenyl)methanol and 4-hydroxy-2,2',3,3',4',5,5',6,6'-nonafluorobiphenyl.

Suitable compounds of the formula (XVIII) are boronic acids and borinic acids, with borinic acids having perfluorinated aryl radicals, for example $(C_6F_5)_2$BOH, being of particular importance. Suitable compounds of the formula (XIX) are dihydroxy compounds in which the divalent carbon-comprising group is preferably halogenated and in particular perfluorinated. An example of such a compound is 4,4'-dihydroxy-2,2',3,3',5,5',6,6'-octafluorobiphenyl hydrate.

Examples of combinations of compounds of the formula (XVI) with compounds of the formula (XVII) or (XIX) are trimethylaluminum/pentafluorophenol, trimethylaluminum/1-bis(pentafluorophenyl)methanol, trimethylaluminum/4-hydroxy-2,2',3,3',4',5,5',6,6'-nonafluorobiphenyl, triethylaluminum/pentafluorophenol, triisobutylaluminum/pentafluorophenol and triethylaluminum/4,4'-dihydroxy-2,2',3,3',5,5',6,6'-octafluorobiphenyl hydrate, with, for example, reaction products of the following type being able to be formed.

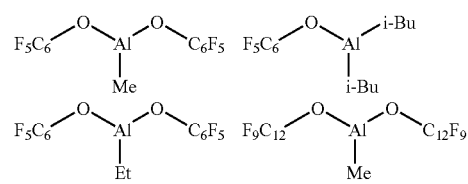

Examples of reaction products from the reaction of at least one compound of the formula (XVI) with at least one compound of the formula (XVIII) are:

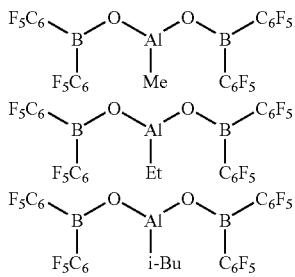

The way in which the components are combined is in principle immaterial.

If appropriate, the reaction products of the reaction of at least one compound of the formula (XVI) with at least one compound of the formula (XVII), (XVIII) or (XIX) and optionally the organic nitrogen base are additionally combined with an organometallic compound of the formula $(X^1)$, (XII), (XIII) and/or (XV) and then reacted with the support to form the supported cocatalyst system.

In a preferred variant, the 1st component, e.g. compounds of the formula (XII), and the 2nd component, e.g. compounds of the formula (XVII), (XVIII) or (XIX), are combined and a support as 3rd component and a base as 4th component are combined separately and the two mixtures are subsequently reacted with one another, preferably in an inert solvent or suspension medium. The supported cocatalyst formed can be freed of the inert solvent or suspension medium before it is reacted with the transition metal coordination compound and optionally a metal compound of the formula (XV) to give the catalyst system.

As further cocatalytically active support component, it is also possible to use the magnesium chloride-alkoxyalkylaluminum supports described in EP 1 568 716 to activate the transition metal compounds of the invention.

It is also possible for the catalyst solid firstly to be prepolymerized with α-olefins, preferably linear $C_2$-$C_{10}$-1-alkenes and in particular ethylene, and the resulting prepolymerized catalyst solid then to be used in the actual polymerization. The mass ratio of catalyst solid used in the prepolymerization to monomer polymerized onto it is usually in the range from 1:0.1 to 1:200.

Furthermore, a small amount of an olefin, preferably an α-olefin, for example vinylcyclohexane, styrene or phenyldimethylvinylsilane, as modifying component, an antistatic or a suitable inert compound such as a wax or oil can be added as additive during or after the preparation of the supported catalyst system. The molar ratio of additives to transition metal compound according to the invention is usually from 1:1000 to 1000:1, preferably from 1:5 to 20:1.

The transition metal compounds of the invention, in particular those of the formula (I) or (Ia), or the catalyst systems comprising them are suitable for the polymerization or copolymerization of olefins, in particular the polymerization of ethene.

The invention further provides a process for preparing polyolefins by polymerization or copolymerization of at least one olefin in the presence of at least one catalyst system as described above, and also a process for preparing olefin oligomers by oligomerization of at least one olefin in the presence of at least one catalyst system of this type. Preference is given to processes for preparing polyolefins or olefin oligomers in which ethylene, optionally together with further α-olefins, is used as olefin.

Olefin oligomers are usually understood to be the dimers, trimers, tetramers, pentamers, hexamers and higher oligomers of an α-olefin.

In general, the catalyst system is used together with a further metal compound of the general formula (XV), which can be different from the metal compound or compounds of the formula (XV) used in the preparation of the catalyst system, for the polymerization or copolymerization of olefins. The further metal compound is generally added to the monomer or the suspension medium and serves to free the monomer of substances which can adversely affect the catalyst activity. It is also possible for one or more further cocatalytic or cation-forming compounds to be additionally added to the catalyst system in the polymerization process.

The olefins can be functionalized, olefinically unsaturated compounds such as ester or amide derivatives of acrylic or methacrylic acid, for example acrylates, methacrylates or acrylonitrile, or nonpolar olefinic compounds, including aryl-substituted α-olefins.

Preference is given to polymerizing olefins of the formula $R^m$—CH=CH—$R^n$, where $R^m$ and $R^n$ are identical or different and are each hydrogen or an organic radical having from 1 to 20 carbon atoms, in particular from 1 to 10 carbon atoms, or $R^m$ and $R^n$ together with the atoms connecting them can form one or more rings.

Examples of such olefins are 1-olefins having from 2 to 40, preferably from 2 to 10, carbon atoms, e.g. ethylene, propylene, 1-butene, 1-pentene, 1-hexene, 1-heptene, 1-octene, 1-decene or 4-methyl-1-pentene or unsubstituted or substituted vinylaromatic compounds such as styrene and styrene derivatives, or dienes such as 1,3-butadiene, 1,4-hexadiene, 1,7-octadiene, 5-ethylidene-2-norbornene, norbornadiene, ethylnorbornadiene or cyclic olefins such as norbornene, tetracyclododecene or methylnorbornene.

The catalyst system of the invention is particularly preferably used for homopolymerizing ethylene or copolymerizing ethylene together with further α-olefins, in particular $C_3$-$C_8$-α-olefins such as propylene, 1-butene, 1-pentene, 1-hexene and/or 1-octene, and/or cyclic olefins such as norbornenes and/or dienes having from 4 to 20 carbon atoms, e.g. 1,4-hexadiene, norbornadiene, ethylidenenorbornene or ethylnorbornadiene, or particularly preferably copolymerizing ethylene with propylene and/or 1-butene. Examples of such copolymers are ethylene-propylene, ethylene-1-butene, ethylene-1-hexene, ethylene-1-octene copolymers and ethylene-propylene-ethylidenenorbornene or ethylene-propylene-1,4-hexadiene terpolymers.

The polymerization can be carried out in a known manner in solution, in suspension, in the gas phase or in a supercritical medium in the customary reactors used for the polymerization of olefins. It can be carried out batchwise or preferably continuously in one or more stages. Solution processes, suspension processes, stirred gas-phase processes or gas-phase fluidized-bed processes are all possible. As solvent or suspension medium, it is possible to use inert hydrocarbons, for example isobutane, or a suitable monomer or comonomer itself. The polymerization using the catalyst system of the invention is preferably carried out in a fluidized-bed gas reactor.

The polymerization can be carried out at temperatures in the range from −60° C. to 300° C. and pressures in the range from 0.5 to 3000 bar. Preference is given to temperatures in the range from 50° C. to 200° C., in particular from 60° C. to 150° C., especially preferably from 70° C. to 120° C., and pressures in the range from 5 to 100 bar, in particular from 15 to 70 bar. The mean residence times are usually from 0.5 to 5 hours, preferably from 0.5 to 3 hours. As molar mass regulators and/or to increase the activity, it is possible to use, for example, hydrogen, diethylzinc, carbon monoxide, carbon dioxide or oxygen in the polymerization. Furthermore, customary additives such as antistatics can also be used. The catalyst system of the invention can be used directly for the polymerization, i.e. it is introduced in undiluted form into the polymerization system, or it is admixed with inert components such as paraffins, oils or waxes to improve meterability.

The ethylene homopolymer or ethylene copolymer prepared using the transition metal compounds of the invention, in particular those of the formula (I) or (Ia), or using the catalyst systems comprising them can also be constituent of a polymer blend. The type of further polymer components in the blend depends on the type of later use of the polymer blend. Blending can, for example, be effected by mixing with one or more additional LLDPEs or HDPEs or LDPEs. On the other hand, the polymer blend can also be obtained by simultaneous polymerization using one or more catalyst systems which are likewise active for the polymerization of olefins. As further catalysts for the preparation of the blend polymers or for the simultaneous polymerization, it is possible to use, in particular, classical Ziegler-Natta catalysts based on titanium, classical Phillips catalysts based on chromium oxides or further single-site catalysts which preferably comprise metallocenes, the "constrained geometry complexes" (cf., for example, EP A 0 416 815 or EP A 0 420 436), chromium single-site complexes as described, for example, in U.S. Pat. No. 6,437,161, nickel and palladium bisimine systems (able to be prepared as described in WO 9803559 A1) or iron and cobal pyridinebisimine compounds (able to be prepared as described in WO 9827124 A1) as transition metal component. To prepare blend polymers, the catalyst system of the invention is preferably used together with catalyst systems comprising a metallocene compound such as bis(n-butylcyclopentadienyl)hafnium dichloride and/or a chromium single-site complex such as (2-methyl-3-phenyl-1-(8-quinolyl)cyclopentadienyl)chromium dichloride as transition metal component. The further catalyst systems can likewise be supported.

The ethylene homopolymer or ethylene copolymer prepared using the inventive transition metal compounds of the formula (I) or (II) or using the catalyst systems comprising them can also form bimodal blends with other olefin polymers, in particular ethylene homopolymers and ethylene copolymers. These can be obtained either by means of the above-described simultaneous presence of a further catalyst suitable for the polymerization of olefins or by subsequent blending of separately prepared polymers or copolymers.

The blends comprising the ethylene homopolymers or ethylene copolymers prepared using the inventive transition metal compounds of the formula (I) or (Ia) or using the catalyst systems comprising them can further comprise two or three other olefin polymers or copolymers. These can be, for example, LDPE grades (blends thereof are described, for example, in DE-A1-19745047), or polyethylene homopolymers (blends thereof are described, for example, in EP-B-100843), LLDPE grades (as described, for example, in EP-8-728160 or WO-A-90/03414) or LLDPE/LDPE grades (WO 95/27005 or EP-B1-662989).

The ethylene copolymers, polymer mixtures and blends can further comprise auxiliaries and/or additives known per se, e.g. processing stabilizers, stabilizers against the effects of light and heat, customary additives such as lubricants, antioxidants, antiblocking agents and antistatics, and also, if appropriate, colorants. A person skilled in the art will be familiar with the type and amount of these additives.

The ethylene homopolymers or ethylene copolymers prepared using the inventive transition metal compounds of the formula (I) or (Ia) or using the catalyst systems comprising them can also be modified subsequently by grafting, crosslinking, hydrogenation, functionalization or other functionalization reactions known to those skilled in the art.

The production of polymer blends can also be carried out by all known methods. This can be achieved, for example, by introducing the powder components into a pelletization apparatus, e.g. a twin-screw kneader (ZSK) or Farrel kneader. Furthermore, a mixture of pelletized polymers can also be processed directly on a film production plant.

The invention is illustrated by the following examples which do not, however, restrict the invention.

EXAMPLES

General

All syntheses and polymerizations were carried out under a protective argon atmosphere. All solvents required were flushed with argon and dried over molecular sieves before use. Indazole-3-carboxylic acid is commercially available (e.g. from Fluka).

Polymer Analysis

Determination of the Melting Point:

The melting point $T_m$ was determined by DSC measurement in accordance with ISO standard 3146 in a first heating phase at a heating rate of 20° C. per minute to 200° C., a dynamic crystallization at a cooling rate of 20° C. per minute down to 25° C. and a second heating phase at a heating rate of 20° C. per minute back to 200° C. The melting point was then the temperature at which the curve of enthalpy versus temperature measured in the second heating phase displayed a maximum.

Gel Permeation Chromatography:

Gel permeation chromatography (GPC) was carried out at 145° C. in 1,2,4-trichlorobenzene using a Waters 150C GPC apparatus. The evaluation of the data was carried out using the software Win-GPC from HS-Entwicklungsgesellschaft für wissenschaftliche Hard-und Software mbH, Ober-Hilbersheim. The calibration of the columns was carried out by means of polyethylene standards having molar masses ranging from 100 to $10^7$ g/mol. Mass average molar mass ($M_w$) and number average molar mass ($M_n$) of the polymers were determined. The Q value is the ratio of mass average ($M_w$) to number average ($M_n$).

Determination of the Limiting Viscosity [η]:

The limiting viscosity, which indicates the limit value of the viscosity number on extrapolation of the polymer concentration to zero, was determined using an automatic Ubbelohde viscometer (Lauda PVS 1) using decalin as solvent at 130° C. in accordance with ISO 1628.

Determination of the Number of Methyl Side Chains and the Density by Means of IR Spectroscopy:

IR spectra were measured on 0.1 mm thick PE films which had been produced by pressing at 180° C. for 15 minutes.

The number of methyl side chains per 1000 carbon atoms of the polymer chain ($CH_3/1000$) was determined by means of IR spectroscopy with the aid of chemical calibration of IR spectra against $^{13}C$-NMR spectra, with the $^{13}C$-NMR spectra being evaluated in respect of the total $CH_3$ group content/1000 carbon atoms and in respect of the content of the defined

EXAMPLES

Example A1

1H-Indazole-3-carbaldehyde (A1)

a) Synthesis of (1H-indazol-3-yl)methanol (A1a)

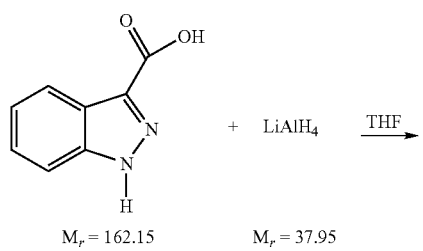

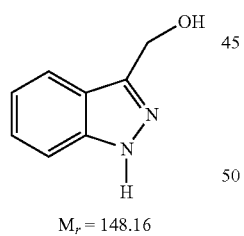

2.31 g (61.05 mmol) of lithium aluminum hydride were stirred in 70 ml of THF$_{abs}$. at room temperature. 6.60 g of indazole-3-carboxylic acid (40.7 mmol) were added a little at a time, with vigorous evolution of gas being observed. After the addition was complete, the yellowish brown suspension was heated to reflux and refluxed overnight. The reaction mixture was brought to room temperature and diluted with THF. 2 ml of H$_2$O, 2 ml of 1N NaOH, 5 ml of H$_2$O were subsequently added dropwise, with vigorous foaming occurring. A milky suspension was formed. The insoluble aluminum salts were centrifuged off to give a clear, slightly yellowish solution. Taking off the solvent on a rotary evaporator gave a colorless product which was dried in a high vacuum. Yield: m=2.83 g (46.9%).

R$_f$=0.59 (ethyl acetate)

Melting point: 135° C.

MS (EI pos): M$^+$=148.1 m/e $^1$H-NMR (300 MHz) in CDCl$_3$: δ=4.78 (d, 2H), 5.22 (t, 1H), 7.08 (1, 1H), 7.32 (t, 1H), 7.47 (d, 1H), 7.83 (d, 1H), 12.78 (s, 1H)

$^{13}$C-NMR: δ=56.78, 110.01, 119.70, 120.63, 121.43, 125.94, 140.98, 145.59 b) Synthesis of 1H-indazole-3-carbaldehyde (A1)

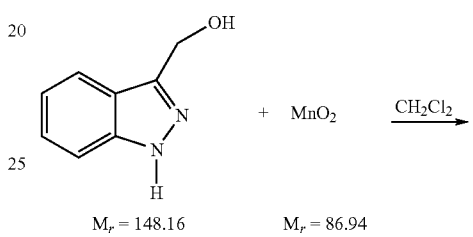

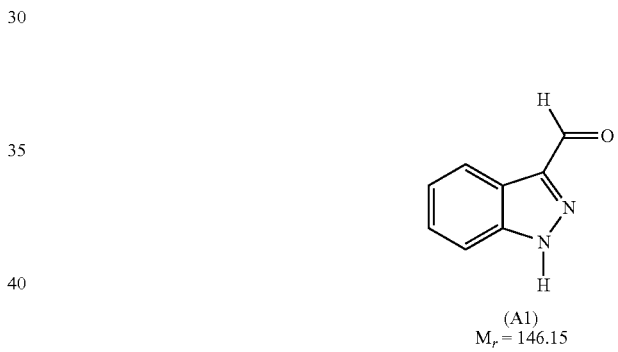

1 g (6.75 mmol) of indazole-3-methanol was stirred with 30 ml of methylene chloride at room temperature. 4.07 g of active manganese dioxide (46.81 mmol) were added and the suspension was stirred for another 48 hours. A spatula tip of manganese dioxide was then added at intervals of 2 to 3 hours until TLC no longer showed any alcohol. The excess manganese dioxide was subsequently separated off by means of deep-bed filtration. The manganese dioxide was collected on a sintered glass suction filter which had been packed densely with silica gel G60 and was washed with ethyl acetate with application of a waterpump vacuum. Taking off the solvent on a rotary evaporator gave a beige product which was dried in a high vacuum. Yield: m=0.845 g (85.7%).

R$_f$=0.82 (ethyl acetate)

Melting point: 130° C.

MS (EI pos): M$^+$=146.1 m/e $^1$H-NMR (300 MHz) in CDCl$_3$: δ=7.38 (t, 1H), 7.50 (t, 1H), 7.59 (d, 1H), 8.33 (d, 1H), 10.32 (s, 1H), 11.07 (s, 1H)

$^{13}$C-NMR: δ=110.39, 121.32, 122.32, 124.58, 128.38, 141.54, 145.11, 187.77

Example B1

1-(1-{[2,6-Dimethylphenylimino]phenylmethyl}-1H-indazol-3-yl)ethanone (B1)

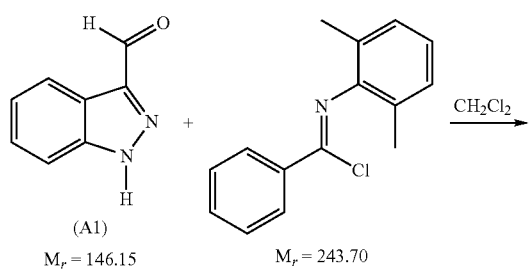

(A1) $M_r = 146.15$   $M_r = 243.70$

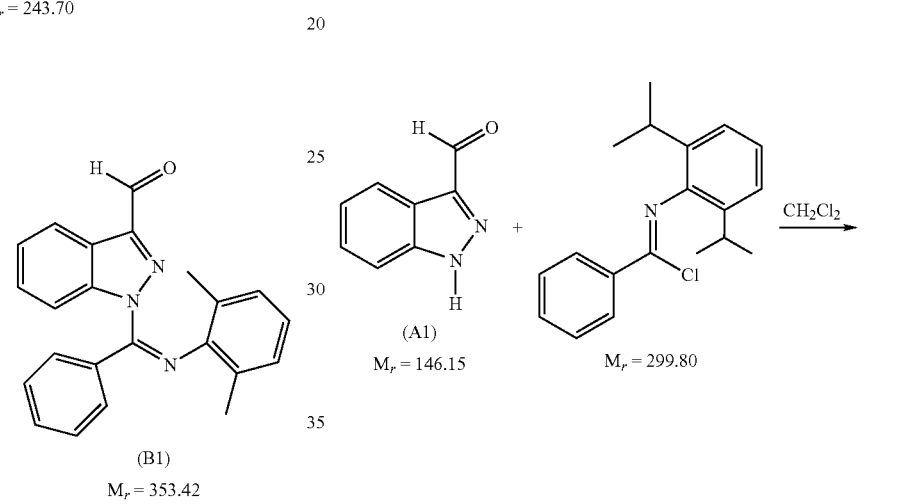

0.700 g of indazole-3-carbaldehyde (4.79 mmol) (A1) was dissolved in 30 ml of absolute methylene chloride. 9.41 ml (4.79 mmol) of a stock solution of imide chloride, having a concentration of 0.124 g/ml was added by means of a syringe. The imide chloride had been prepared from the corresponding carboxamide and thionyl chloride as described in WO 2005/030813. 660 μl of triethylamine (4.79 mmol) were added by means of a syringe. The mixture became an intense yellow color within a few minutes. The solution was stirred overnight at room temperature. The intense yellow solution was washed twice with water in a separating funnel, the organic phase was separated off and dried over magnesium sulfate. Taking off the solvent gave a viscous yellow oil. The crude product was purified via a short column, with the target product eluting most quickly.

Column material: silica gel G60; column length: 16 cm; column diameter: 2.5 cm; eluent: chloroform A yellow oil was initially obtained and this was digested in ether. The target product begins to crystallize out immediately. The ether was siphoned off and the product was dried in a high vacuum. Yield: m=0.846 g (50%); appearance: yellow crystals.

$R_f$=0.76 (chloroform)

Melting point: 170° C.

MS (FAB): [M+H]$^+$=354, 1 m/e $^1$H-NMR (300 MHz) in CDCl$_3$: δ=2.15 (s, 6H), 6.83-7.07 (m, 3H), 7.26-7.69 (m, 7H), 8.43 (d, 1H), 8.68 (d, 1H), 10.21 (s, 1H)

$^{13}$C-NMR: δ=18.99, 116.37, 122.36, 123.47, 123.82, 126.02, 126.84, 128.23, 128.32, 129.49, 130.79, 131.81, 141.80, 145.16, 145.55, 154.15, 187.92

Example B2

1-(1-{[2,6-Diisopropylphenylimino]phenylmethyl}-1H-indazol-3-yl)ethanone (B2)

The synthesis of (B2) was carried out by a method analogous to Example B1 using 520 mg (3.558 mmol) of aldehyde (A1), 1.067 g (3.558 mmol) of imide chloride and 300 mg (3.558 mmol) of triethylamine. Yield: m=0.682 g (47%); appearance: yellow crystals.

$R_f$=0.82 (chloroform)

Melting point: 105-107° C.

$^1$H-NMR (300 MHz) in CDCl$_3$: δ=0.96 (d, 6H), 1.17 (d, 6H), 3.00 (m, 2H), 7.05-7.65 (m, 10H), 8.44 (d, 1H), 8.62 (d, 1H), 10.22 (s, 1H)

$^{13}$C-NMR: δ=22.22, 24.67, 28.80, 28.93, 115.94, 119.65, 122.38, 123.37, 124.54, 125.99, 128.11, 128.20, 129.58, 130.08, 136.91, 141.85, 142.00, 145.04, 148.50, 153.23, 187.92

Example B3

Synthesis of Building Block (B3)

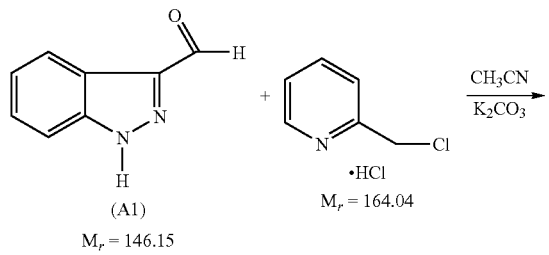

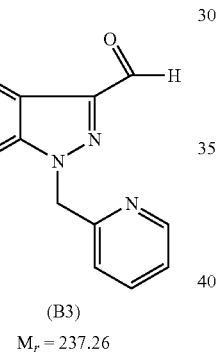

600 mg of aldehyde (4.11 mmol) (A1) were dissolved in 35 ml of acetonitrile. 664 mg of 2-picolyl chloride hydrochloride (4.05 mmol) and 1.120 g of potassium carbonate were added. The suspension was refluxed for 20 hours and, after cooling, the potassium carbonate was collected in a paper filter. The solvent was taken off by means of a rotary evaporator. The crude product obtained was purified by column chromatography.

Eluent mixture: ether/THF=4:1; stationary phase: silica gel G60; column length: 12 cm; column diameter: 3.5 cm Yield: m=0.700 g (72.9%); appearance: light-yellow powder $R_f$=0.60 (ether/THF=4:1)

Melting point: 78-79° C.

$^1$H-NMR (300 MHz) in CDCl$_3$: δ=5.79 (s, 2H), 6.98 (d, 1H), 7.18 (dd, 1H), 7.40 (dd, 1H), 7.31 (dd, 1H), 7.46 (dd, 1H), 7.58 (dd, 1H), 8.28 (d, 1H), 8.56 (d, 1H), 10.24 (s, 1H)

$^{13}$C-NMR: δ=56.07, 110.32, 121.95, 122.45, 123.39, 124.51, 128.00, 137.47, 141.43, 143.73, 149.97, 155.46, 187.22

Example B4

Synthesis of Building Block (B4)

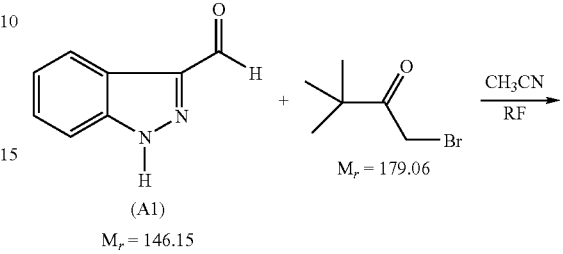

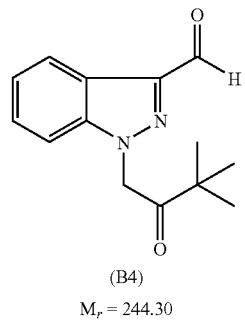

600 mg of 3-formylindazole (3.421 mmol) (A1) were dissolved in 35 ml of acetonitrile.

612 mg of 1-bromopinacolone (3.421 mmol) and 474 µl of triethylamine were added. The solution was refluxed for 20 hours and, after cooling, the solution was diluted with water and transferred to a separating funnel. The aqueous solution was extracted with methylene chloride. The organic phase was then washed firstly with water and subsequently once with a saturated NaCl solution. The solution was dried over sodium sulfate and filtered through a paper filter. After the major part of the solvent had been taken off on a rotary evaporator, the product was dried in a high vacuum.

Yield: m=0.819 g (98%); appearance: yellowish brown powder $R_f$=0.30 (ether/hexane=1:1)

Melting point: 81-83° C.

IR: 1678 cm$^{-1}$ (C=O); 1721 cm$^{-1}$ (C=O)

$^1$H-NMR (300 MHz) in CDCl$_3$ [ppm]: δ=1.29 (s, 9H), 5.43 (s, 2H), 7.19 (d, 1H), 7.30 (m, 1H), 7.39 (m, 1H), 8.26 (d, 1H), 10.19 (s, 1H).

$^{13}$C-NMR: δ=26.43, 43.85, 54.23, 109.45, 122.26, 122.44, 124.34, 127.98, 141.91, 143.87, 187.05, 207.39.

Example B5

Synthesis of Building Block (B5)

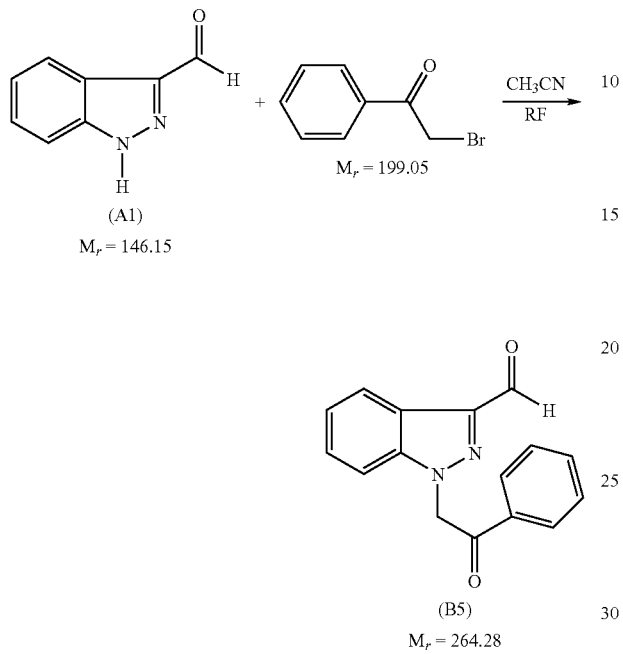

The synthesis of (B5) is carried out by a method analogous to Example B4.

Example C1

Synthesis of Ligand (C1)

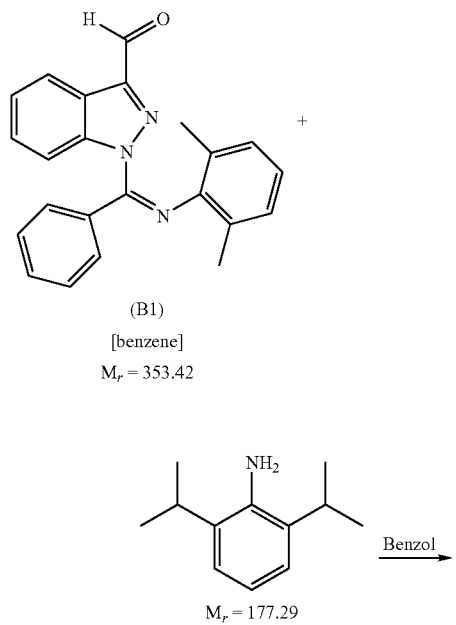

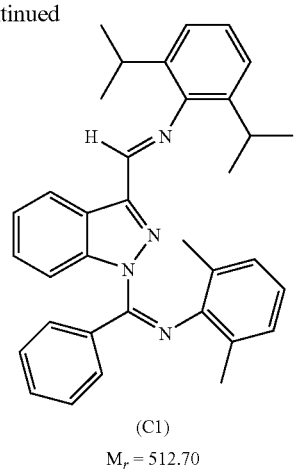

1.166 g of aldehyde (3.30 mmol) (B1) were dissolved in 25 ml of benzene. 623 μl of 2,6-diisopropylaniline (3.30 mmol) were added. The mixture was acidified with 3 drops of trifluoroacetic acid and refluxed using a water separator for 24 hours. The yellow solution was washed with $H_2O$ until neutral and dried over magnesium sulfate. Taking off the solvent by means of a rotary evaporator left a viscous yellow residue which became solid after foaming with ether. The residue was taken up in a little ether and placed in a refrigerator. Yellow crystals were formed overnight. The supernatant solution was removed by means of a pipette and the product was dried in a high vacuum. Yield: m=0.915 g (56%); appearance: yellow crystals.

$R_f$=0.87 (ether/hexane=1:1)

Melting point: 162-164° C.

MS (FAB): $[M+H]^+$=513.29 m/e $^1$H-NMR (300 MHz) in $CDCl_3$: δ=1.22 (s, 6H), 1.24 (s, 6H), 2.18 (s, 6H), 3.10 (m, 2H), 6.87-7.05 (m, 3H), 7.13-7.43 (m, 8H), 7.53 (t, 1H), 7.65 (t, 1H), 8.51 (s, 1H), 8.71 (d, 1H), 8.76 (d, 1H)

$^{13}$C-NMR: δ=19.08, 23.72, 28.33, 116.30, 123.28, 123.50, 123.77, 124.58, 124.68, 125.15, 127.09, 128.09, 128.28, 129.12, 129.67, 130.53, 132.29, 137.37, 141.85, 145.25, 146.03, 149.47, 154.12, 157.29

Example C2

Synthesis of Ligand (C2)

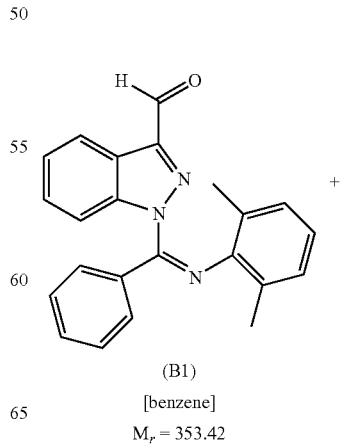

-continued

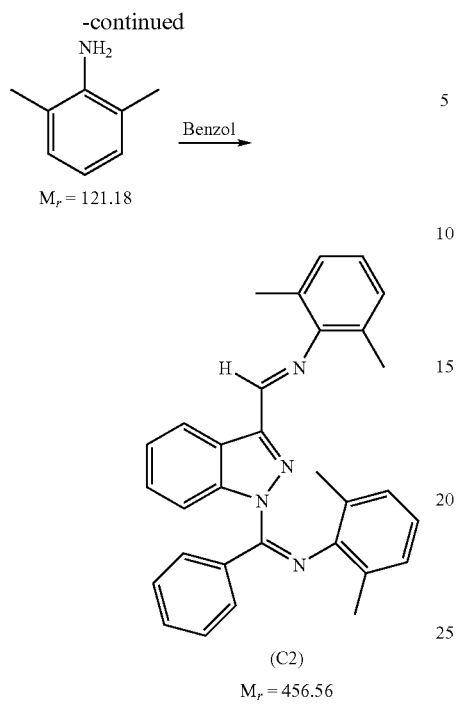

(C2)
$M_r = 456.56$

The synthesis was carried out by a method analogous to C1 using 571 mg (1.617 mmol) of aldehyde (B1) and 200 µl (1.617 mmol) of 2,6-dimethylaniline as starting materials. Yield: m=0.633 g (85.7%); appearance: yellow crystals.

$R_f$=0.85 (ether/hexane=1:1)

Melting point: 146-148° C.

$^1$H-NMR (300 MHz) in CDCl$_3$: δ=2.16 (s, 6H), 2.23 (s, 6H), 6.87-7.65 (m, 13H), 8.52 (s, 1H), 8.69 (d, 1H), 8.75 (s, 1H)

$^{13}$C-NMR: δ=18.74, 19.05, 116.24, 123.48, 123.80, 124.31, 124.48, 125.07, 127.08, 127.14, 128.09, 128.24, 128.44, 129.12, 129.61, 130.50, 132.32, 141.80, 145.32, 146.01, 151.31, 154.09, 157.73

Example C3

Synthesis of Ligand (C3)

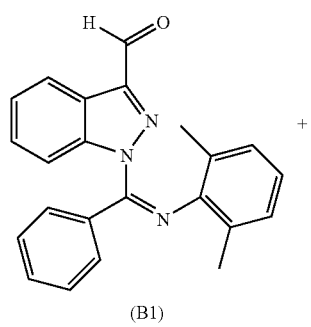

(B1)
[benzene]
$M_r = 353.42$

-continued

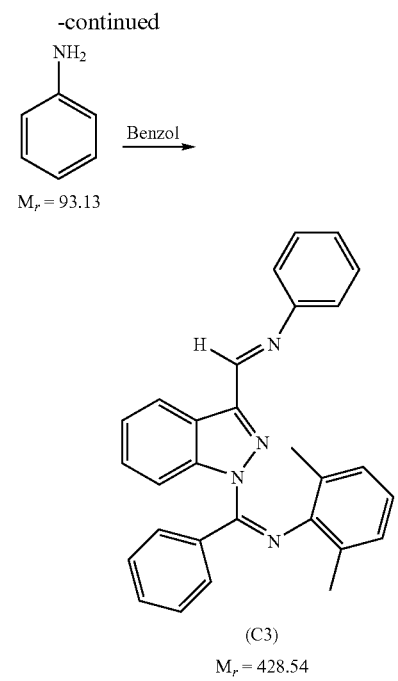

(C3)
$M_r = 428.54$

The synthesis was carried out by a method analogous to Example C1 using 465 mg (1.317 mmol) of aldehyde (B1) and 122.6 µl (1.317 mmol) of aniline as starting materials. Yield: m=0.557 g (98%); appearance: yellow crystals $R_f$=0.82 (ether/hexane=1:1)

Melting point: 135-137° C.

MS (FAB): [M+H]$^+$=429.2 m/e $^1$H-NMR (300 MHz) in CDCl$_3$: δ=2.17 (s, 6H), 6.68-7.64 (m, 15H), 8.70 (d, 1H), 8.77 (d, 1H), 8.82 (s, 1H)

$^{13}$C-NMR: δ=19.06, 115.39, 115.14, 121.38, 123.47, 123.76, 125.03, 126.88, 127.07, 128.08, 128.23, 128.64, 129.13, 129.50, 129.55, 130.47, 141.77, 145.57, 146.00, 151.86, 154.10, 154.71

Example C4

Synthesis of Ligand (C4)

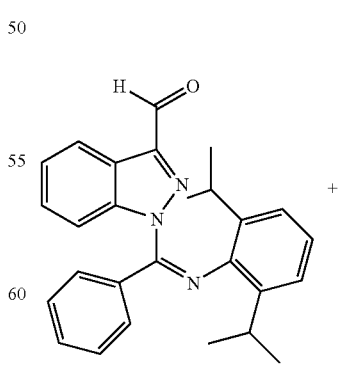

(B2)
[benzene]
$M_r = 409.53$

Example C5

Synthesis of Ligand (C5)

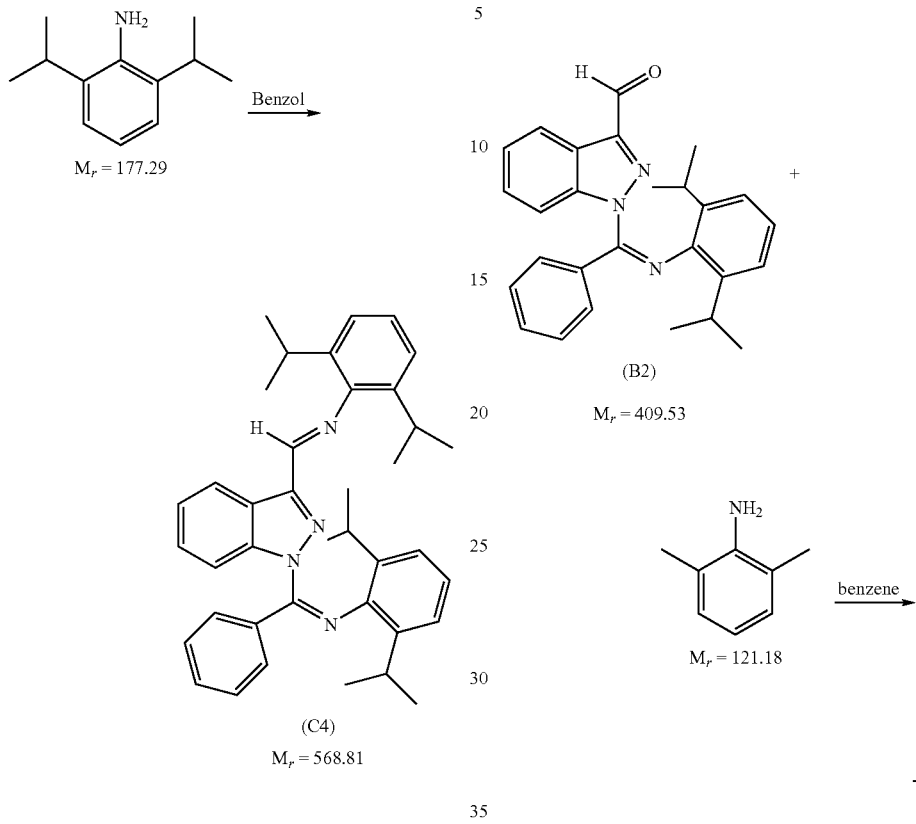

0.868 g of aldehyde (2.119 mmol) (B2) was dissolved in 25 ml of benzene. 400 μl of 2,6-diisopropylaniline (2.119 mmol) were added. The mixture was acidified with 3 drops of trifluoroacetic acid and refluxed using a water separator for 24 hours. The yellow solution was washed with $H_2O$ until neutral and dried over magnesium sulfate. Taking off the solvent by means of a rotary evaporator left a viscous yellow residue which became solid after foaming with ether. The crude product was purified by deep-bed filtration. A sintered glass suction filter packed with silica gel G60 was used for this purpose.

The target product eluted virtually with the solvent front in an eluent mixture of ether/hexane 1:1. Taking off the solvent on a rotary evaporator and drying in a high vacuum gave a solid, yellow reaction product. Yield: m=0.900 g (74.6%); appearance: yellow crystals $R_f$=0.87 (ether/hexane=1:1)

Melting point: 165-167° C.

MS (FAB): $[M+H]^+$=569.36 m/e $^1$H-NMR (300 MHz) in $CDCl_3$: δ=0.91 (d, 3H), 0.99 (d, 6H), 1.23 (d, 12H), 1.32 (d, 3H), 2.91-3.17 (m, 4H), 7.07-7.73 (m, 12H), 8.51 (s, 1H), 8.70 (d, 1H), 8.76 (d, 1H)

$^{13}$C-NMR: δ=22.25, 23.70, 24.73, 28.25, 28.31, 28.77, 28.94, 115.94, 118.84, 119.67, 123.08, 123.27, 123.74, 124.17, 125.14, 128.02, 129.24, 130.25, 130.36, 137.11, 137.36, 141.86, 142.96, 145.06, 149.47, 153.23, 157.27

The synthesis was carried out by a method analogous to Example C1 using 247 mg (0.603 mmol) of aldehyde (B2) and 75 μl (0.603 mmol) of 2,6-dimethylaniline as starting materials. Yield: m=0.190 g (61%); appearance: yellow crystals.

$R_f$=0.86 (ether/hexane=1:1)

$^1$H-NMR (300 MHz) in $CDCl_3$: δ=0.90-1.27 (m, 12H), 2.24 (s, 6H), 3.09 (m, 2H), 6.98-7.72 (m, 13H), 8.53 (s, 1H), 8.68 (d, 1H), 8.77 (d, 1H)

$^{13}$C-NMR: δ=18.76, 22.26, 24.12, 24.42, 24.71, 28.80, 29.32, 115.87, 123.28, 123.82, 124.20, 124.31, 125.04, 127.16, 128.08, 128.16, 128.87, 129.33, 129.35, 130.22, 133.31, 137.13, 141.85, 145.19, 147.44, 151.33, 153.20, 157.76

Example C6

Synthesis of Ligand (C6)

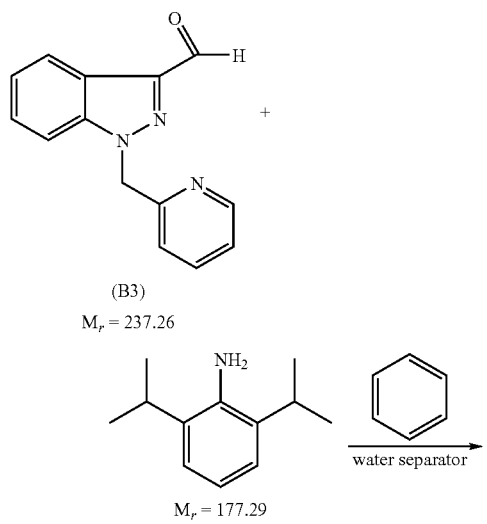

264 mg of aldehyde (1.112 mmol) (B3) were dissolved in 20 ml of benzene and refluxed together with 197 mg of 2,6-diisopropylaniline (1.112 mmol) and 3 drops of trifluoroacetic acid for 48 hours. The yellow solution was washed until neutral and dried over magnesium sulfate. After the major part of the solvent had been taken off, the crude product was briefly dried in a high vacuum, giving a yellow oil. The crude product obtained was purified by column chromatography.

Eluent: ether; stationary phase: silica gel G60; column length: 11 cm;

column diameter: 2.5 cm

Yield m=299 mg (67.8%); appearance: light-yellow powder $R_f$=0.57 (ether)

Melting point: 110-111° C.

$^1$H-NMR (300 MHz) in CDCl$_3$: δ=1.22 (d, 12H), 3.13 (sept, 2H), 5.84 (s, 2H), 7.05 (d, 1H), 7.15 (dd, 1H), 7.21-7.24 (m, 3H), 7.34 (dd, 1H), 7.47 (dd, 2H), 7.63 (dd, 1H), 8.59 (s, 1H), 8.63 (d, 2H)

$^{13}$C-NMR: δ=23.81, 28.27, 55.69, 109.96, 121.92, 123.01, 123.22, 123.30, 123.82, 124.42, 124.43, 127.74, 137.44, 137.72, 141.52, 143.01, 149.72, 149.89, 156.27, 156.93

Example C7

Synthesis of Ligand (C7)

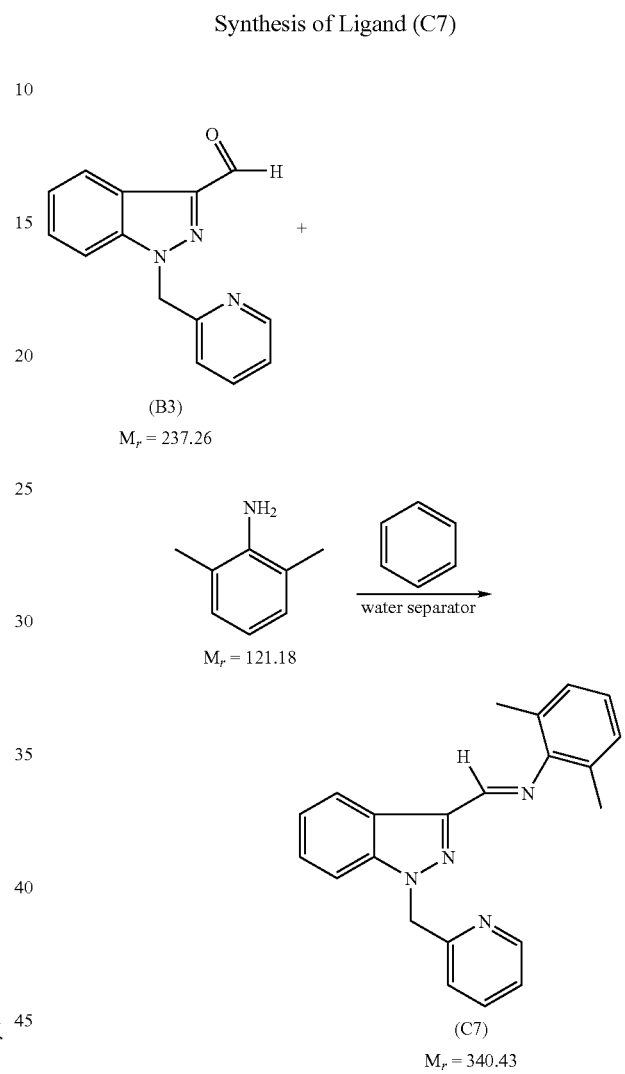

350 mg of aldehyde (1.48 mmol) (B3) were dissolved in 20 ml of benzene and refluxed together with 179 mg of 2,6-dimethylaniline (1.48 mmol) and 3 drops of trifluoroacetic acid for 20 hours. The yellow solution was washed until neutral and dried over magnesium sulfate. After the major part of the solvent had been taken off, the crude product was briefly dried in a high vacuum, giving a yellow oil. The crude product obtained was purified by column chromatography.

Eluent mixture: ether/THF=4:1; stationary phase: silica gel G60; column length: 12 cm;

column diameter: 2.5 cm

Yield m=345 mg (68.4%); appearance: light-yellow oil $R_f$=0.68 (ether/THF=4:1)

$^1$H-NMR (300 MHz) in CDCl$_3$: δ=2.25 (s, 6H), 5.82 (s, 2H), 7.01 (d, 2H), 7.12 (d, 2H), 7.21 (dd, 1H), 7.33 (dd, 1H), 7.46 (d, 2H), 7.60 (dd, 1H), 8.61 (s, 2H), 8.64 (s, 1H)

$^{13}$C-NMR: δ=18.77, 55.58, 109.86, 121.81, 122.90, 123.14, 123.83, 124.03, 127.42, 127.71, 128.40, 137.37, 141.49, 143.07, 149.86, 151.54, 156.29, 157.44

Example C8

Synthesis of Ligand (C8)

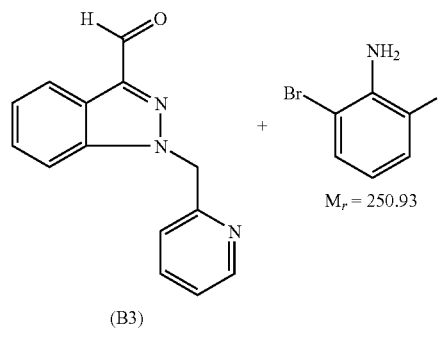

(B3)
M$_r$ = 237.26

(C8)
M$_r$ = 470.17

300 mg of aldehyde (1.26 mmol) (B3) were dissolved in 30 ml of benzene and refluxed together with 524 mg of 2,6-dibromoaniline (2.09 mmol) and 3 drops of trifluoroacetic acid for 17 days using a water separator. The yellow solution was washed until neutral and dried over sodium sulfate. After the major part of the solvent had been taken off, the crude product was briefly dried in a high vacuum, giving a yellowish brown oil. The crude product obtained was purified by column chromatography. Yield: m=295 mg (49.7%); appearance: light-yellow powder R$_f$=0.35 (ether)

Melting point: 46-48° C.

IR: 1632 cm$^{-1}$ (C=N)

$^1$H-NMR (300 MHz) in CDCl$_3$: δ=5.82 (s, 2H), 6.86 (t, 1H), 7.01 (d, 1H), 7.18-7.22 (m, 1H), 7.31-7.36 (m, 1H), 7.41-7.48 (m, 2H), 7.56-7.62 (m, 3H), 8.60-8.65 (m, 2H), 8.68 (s, 1H)

$^{13}$C-NMR: δ=55.59, 109.79, 115.24, 121.73, 122.98, 123.05, 123.44, 123.70, 126.10, 127.66, 132.32, 137.27, 141.36, 142.11, 149.67, 149.74, 155.89, 160.89

MS (FAB pos): (M+H)$^+$=470.94

Example C9

Synthesis of Ligand (C9)

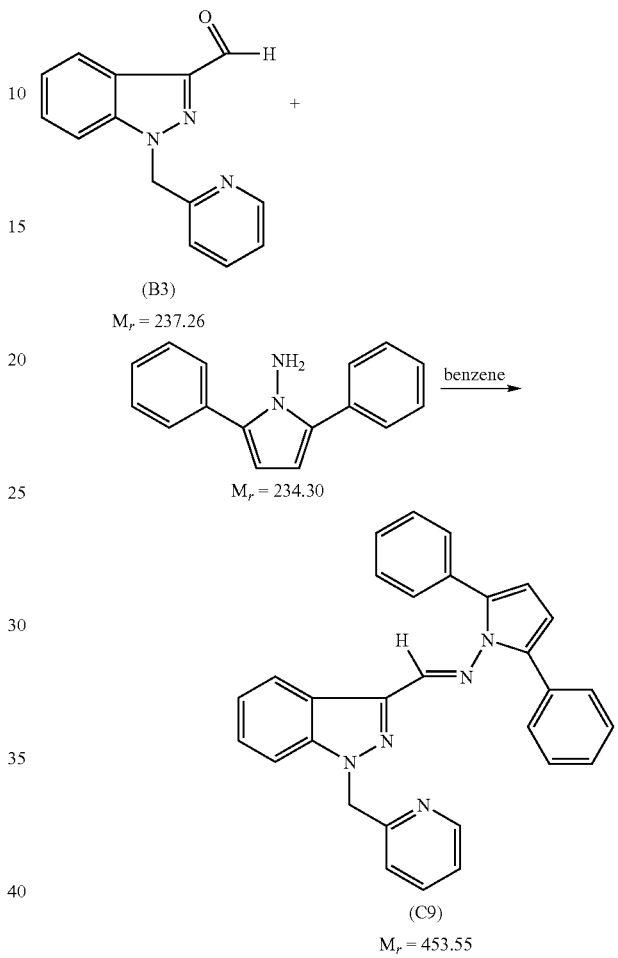

(B3)
M$_r$ = 237.26

M$_r$ = 234.30

(C9)
M$_r$ = 453.55

Reaction Procedure:

300 mg of aldehyde (1.264 mmol) (B3) were dissolved in 20 ml of benzene and refluxed together with 296 mg of 2,5-diphenylpyrrol-1-ylamine (1.264 mmol) and 4 drops of trifluoroacetic acid for 72 hours. The reaction solution was washed twice with 5% strength aqueous sodium hydroxide solution, then twice with water and dried over sodium sulfate. The filtered solution was evaporated on a rotary evaporator and briefly dried in a high vacuum, giving a yellow oil. The crude product obtained was purified by column chromatography.

Eluent: ether: THF=4:1; stationary phase: silica gel G60; column length: 12 cm;

column diameter: 2.5 cm

Yield m=318 mg (55.5%); appearance: yellow powder

R$_f$=0.37 (ether: THF=4:1)

Melting point: 55° C.

$^1$H-NMR (300 MHz) in CDCl$_3$: δ=5.69 (s, 2H), 6.49 (s, 2H), 6.82 (d, 1H), 7.17 (at, 1H), 7.24-7.43 (m, 9H), 7.53 (d*t, 1H), 7.64-7.68 (m, 4H), 8.37-8.40 (m, 2H), 5.57 (d, 1H)

$^{13}$C-NMR: δ=55.46, 109.59, 109.93, 121.70, 122.44, 123.14, 123.19, 123.70, 126.87, 127.74, 128.69. 128.75, 132.58, 132.89, 137.34, 140.30, 141.37, 149.74, 156.15, 156.83

Example D1

Synthesis of Complex (D1)

Example D2

Synthesis of Complex (D2)

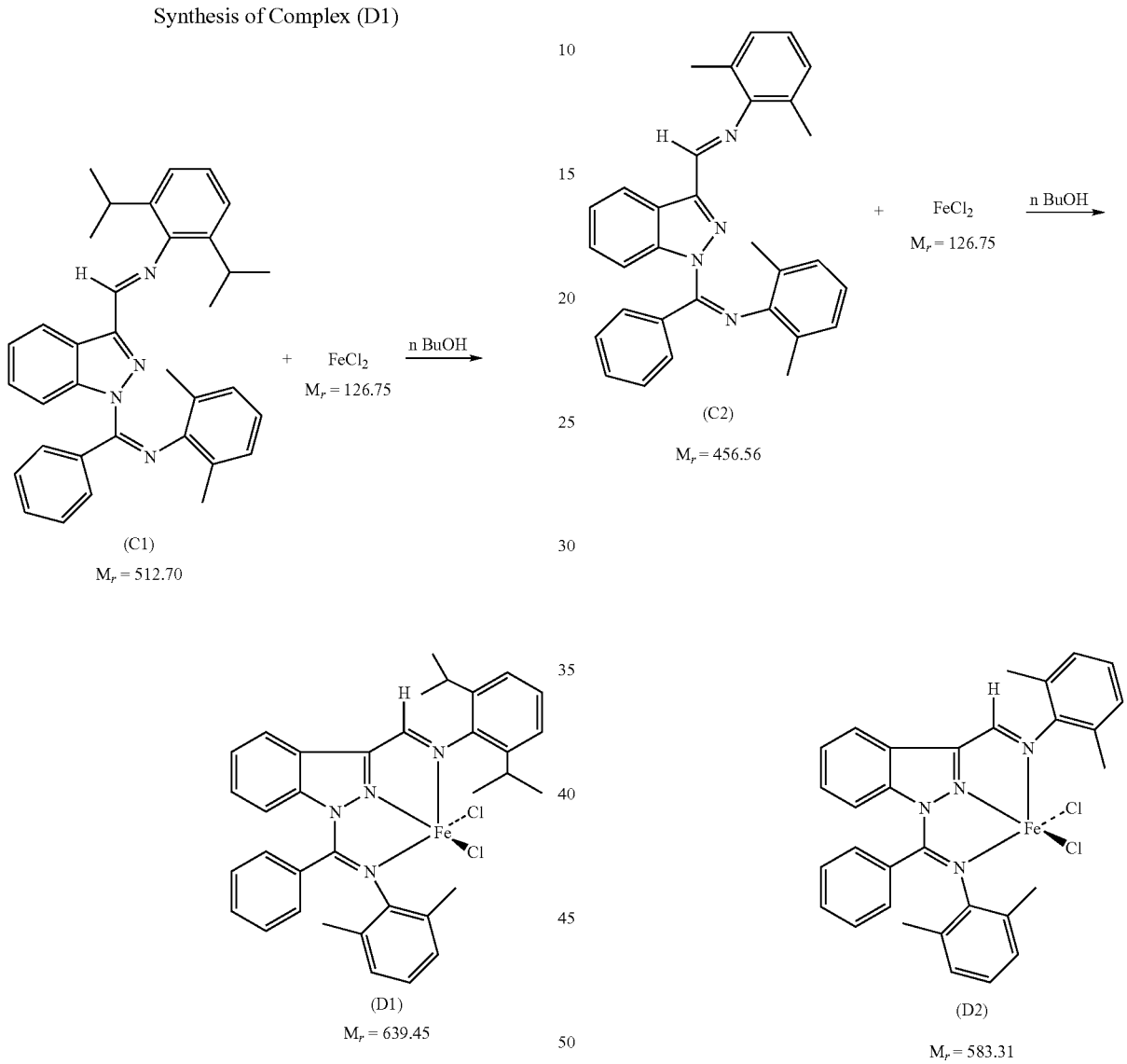

142 mg of ligand (0.277 mmol) (C1) were stirred in 10 ml of n-butanol. 35 mg of FeCl$_2$ (0.277 mmol) were dissolved in 20 ml of butanol by heating and added to the suspension of the ligand, with the mixture becoming brown immediately after the addition. The mixture was subsequently stirred at 95° C. for 15 hours, with no deepening of the color and no color change being able to be observed. For this reason, the mixture was subsequently refluxed for 24 hours. An intensely dark green solution was formed. The solvent was taken off in a high vacuum and the powder which remained was dried in a high vacuum for a number of hours.

Appearance: green powder, with a small proportion of brown material;

decomposition point: 180-182° C.

500 mg of ligand (1.095 mmol) (C2) were stirred in 20 ml of n-butanol. 139 mg of FeCl$_2$ (1.095 mmol) were dissolved in 20 ml of butanol by heating and added to the suspension of the ligand, with the mixture becoming brown immediately after the addition. The mixture was subsequently stirred at 80° C. for 15 minutes and then at room temperature for 18 hours. The solvent was taken off in a high vacuum and the residue was washed twice with absolute ether. The powder which remained was dried in a high vacuum for a number of hours.

Appearance: rust-brown powder

Example D3

Synthesis of Complex (D3)

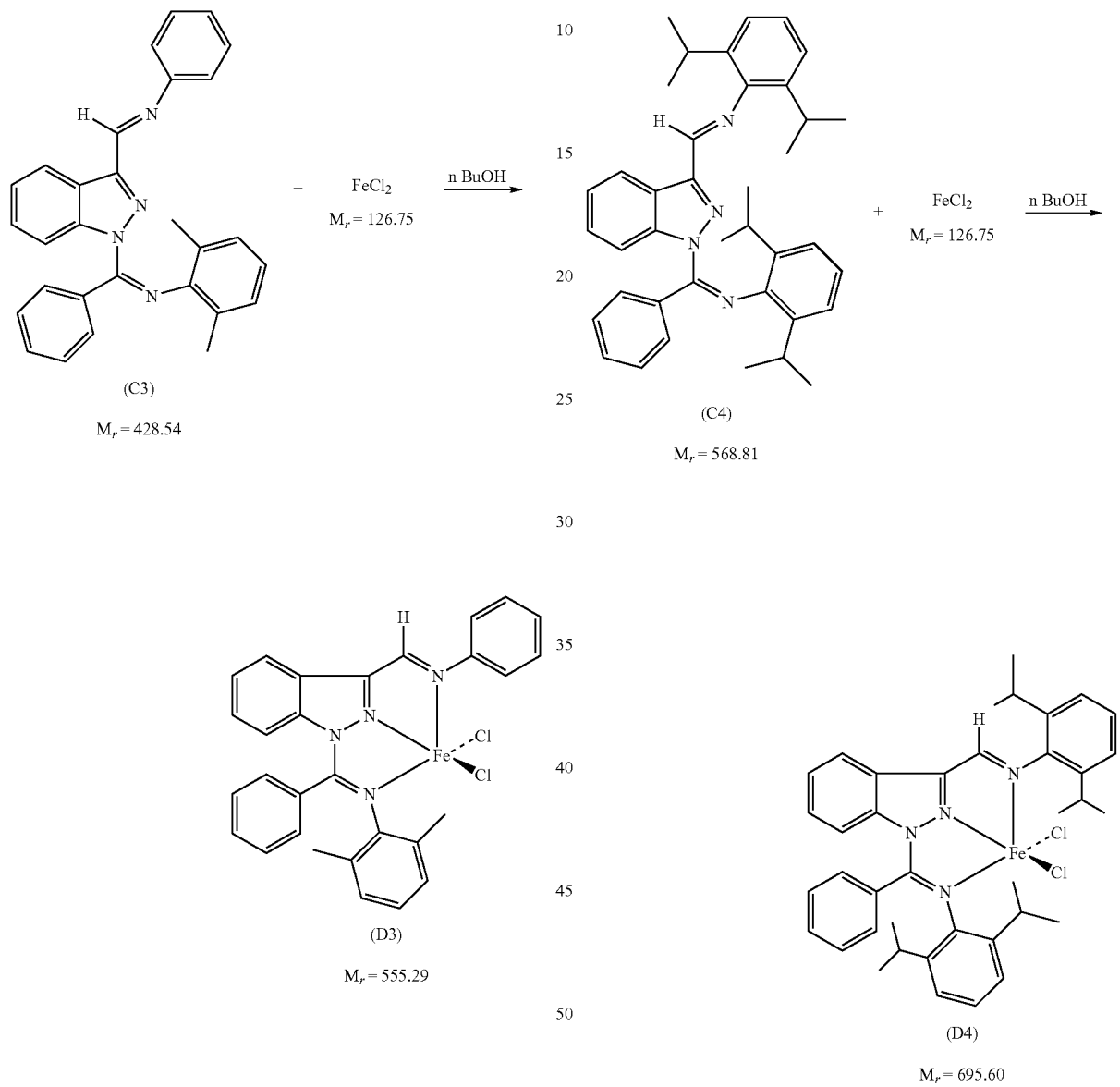

Example D4

Synthesis of Complex (D4)

400 mg of ligand (0.933 mmol) (C3) were stirred in 20 ml of n-butanol. 118 mg of FeCl$_2$ (0.933 mmol) were dissolved in 20 ml of butanol by heating and added to the suspension of the ligand, with the mixture becoming brown immediately after the addition. The mixture was subsequently stirred at 80° C. for 15 minutes and then at room temperature for 17 hours. The solvent was taken off in a high vacuum and the residue was washed three times with absolute ether. The powder which remained was dried in a high vacuum for a number of hours.

Appearance: brown powder
Decomposition point: 172° C.
MS (FAB): [M+H]$^+$=1039.4 m/e 220 mg of ligand (0.387 mmol) (C4) were stirred in 25 ml of n-butanol by means of a magnetic stirrer. 49 mg of FeCl$_2$ (0.387 mmol) were added to the solution. The mixture was subsequently refluxed for 38 hours. After refluxing for a number of hours a dark blue solution was obtained. The solvent was taken off in a high vacuum. The powder which remained was dried in a high vacuum for a number of hours.

Appearance: green powder
Decomposition point: 125-127° C.

Example D5

Synthesis of Complex (D5)

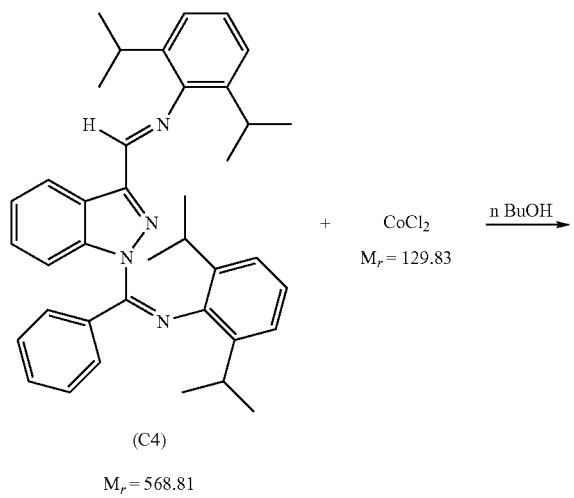

Example D6

Synthesis of Complex (D6)

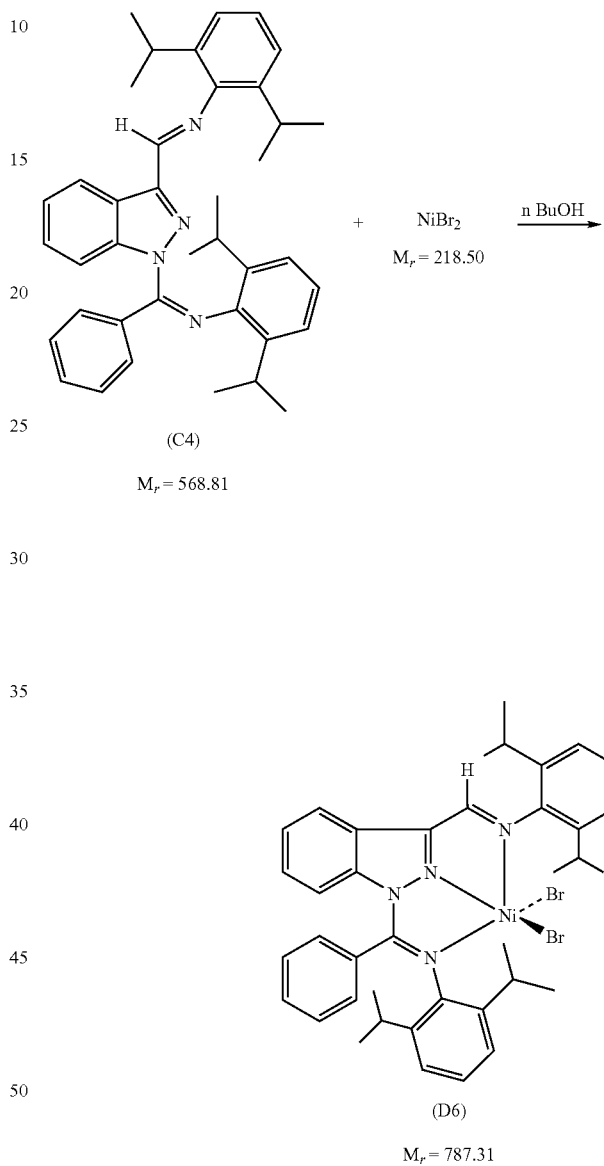

227 mg of ligand (0.400 mmol) (C4) were stirred in 25 ml of n-butanol. 49 mg of CoCl$_2$ (0.400 mmol) were added to the solution. The mixture was subsequently refluxed for 46 hours. After refluxing for a number of hours, a bluish green solution was formed. The solvent was taken off in a high vacuum. The powder which remained was dried in a high vacuum for a number of hours.

Appearance: green powder

Decomposition point: 158-160° C.

229 mg of ligand (0.403 mmol) (C4) were stirred in 25 ml of n-butanol. 88 mg of NiBr$_2$ (0.403 mmol) were added to the solution. The mixture was subsequently refluxed for 24 hours. After refluxing for a number of hours, a brown solution was formed. The solvent was taken off in a high vacuum. The powder which remained was dried in a high vacuum for a number of hours.

Appearance: light-brown powder

Decomposition point: 180° C.

Example D7

Synthesis of Complex (D7)

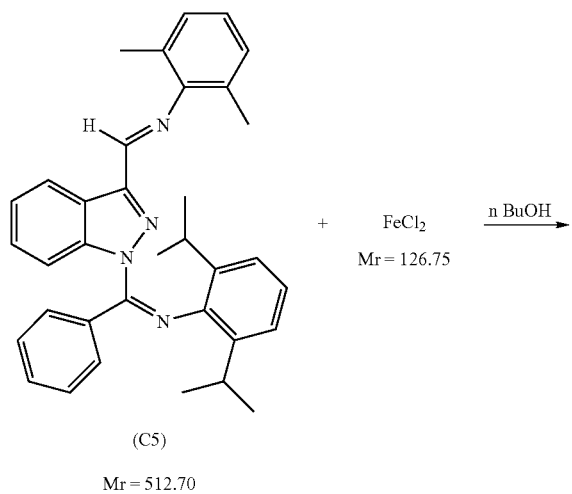

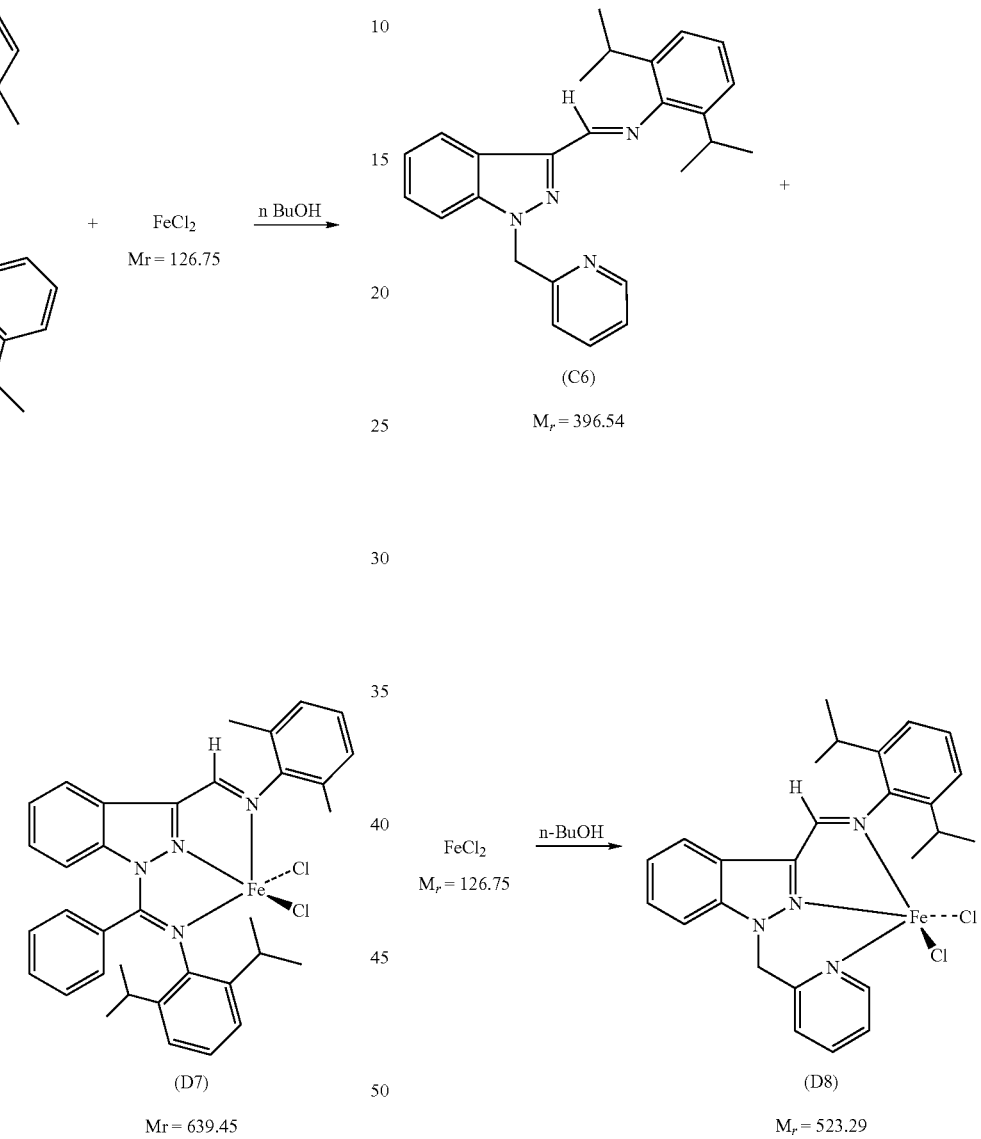

164 mg of ligand (0.302 mmol) (C5) were stirred in 20 ml of n-butanol. 40.5 mg of $FeCl_2$ (0.302 mmol) were dissolved in 20 ml of butanol by heating and added to the suspension of the ligand. The mixture was subsequently refluxed for 17 hours, with the mixture becoming green after only a short time. A dark blue solution was formed overnight.

The solvent was taken off in a high vacuum. The powder which remained was dried in a high vacuum for a number of hours.

Appearance: green powder

Example D8

Synthesis of Complex (D8)

102 mg of ligand (0.257 mmol) (C6) were stirred in 25 ml n-butanol. 33 mg of $FeCl_2$ (0.257 mmol) were dissolved in 25 ml of n-butanol with heating and added to the solution, with the mixture spontaneously becoming yellow. The mixture was subsequently stirred at 80° C. for 24 hours. After heating for a number of hours, a dark green solution was formed. The solid was taken off in a high vacuum. The powder which remained was dried in a high vacuum for a number of hours.

Appearance: green powder

Melting point: 108-110° C.

Example D9

Synthesis of Complex (D9)

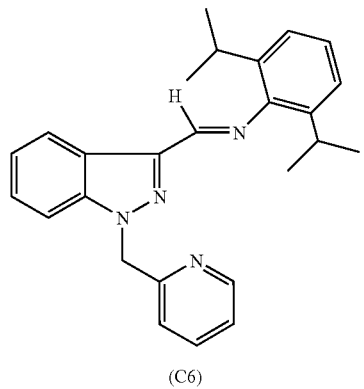

(C6)
Mr = 396.54

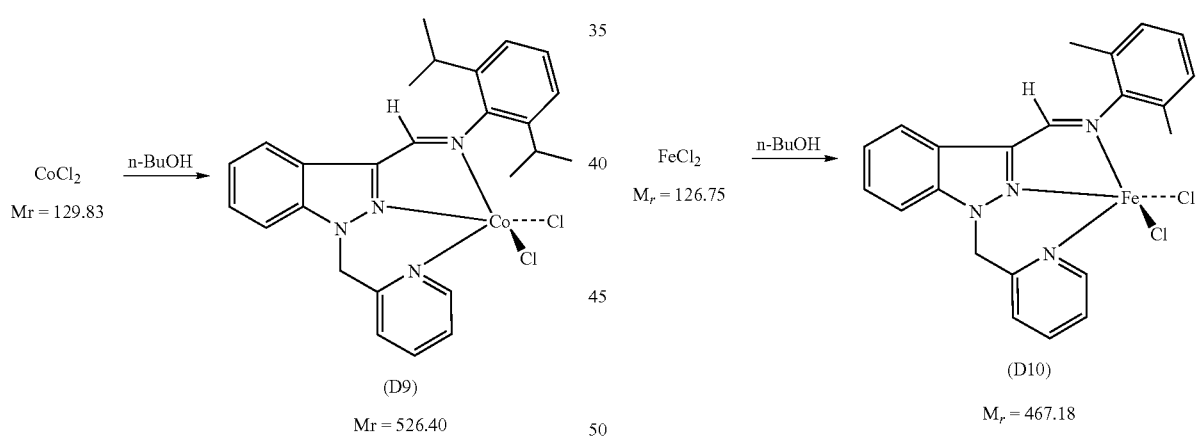

(D9)
Mr = 526.40

149 mg of ligand (0.376 mmol) (C6) were stirred in 25 ml n-butanol. 49 mg of $CoCl_2$ (0.376 mmol) were dissolved in 25 ml of n-butanol with heating and added to the solution, with the mixture spontaneously becoming green. The mixture was subsequently refluxed for 24 hours. After refluxing for a number of hours, a bluish green solution was formed. The solvent is taken off in a high vacuum. The powder which remains was dried in a high vacuum for a number of hours. The complex was washed with absolute ether and dried again.

Appearance: green powder

Melting point: commencing at 210° C. and extending over 25° C. without a color change

Example D10

Synthesis of Complex (D10)

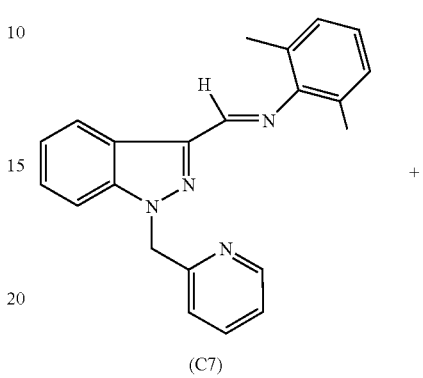

(C7)
$M_r$ = 340.43

(D10)
$M_r$ = 467.18

98 mg of ligand (0.288 mmol) (C7) were stirred in 25 ml of n-butanol. 37 mg of $FeCl_2$ (0.288 mmol) were dissolved in 25 ml of n-butanol with heating and added to the solution, with the mixture spontaneously becoming yellow. The mixture was subsequently stirred at 100° C. for 24 hours. After heating for a number of hours, a green solution was formed. The solvent was taken off in a high vacuum. The powder which remained was dried in a high vacuum for a number of hours.

Appearance: green powder

Melting point: commencing at 80° C., extended over 30° C. with the color changing from green to brown

Example D11

Synthesis of Complex (D11)

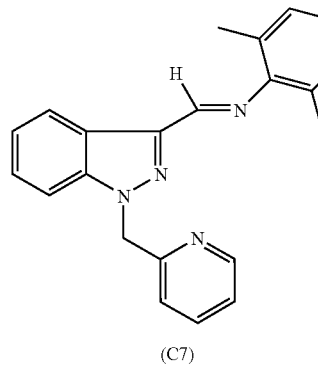

(C7)
$M_r = 340.43$

CoCl$_2$  $\xrightarrow{\text{n-BuOH}}$
Mr = 129.83

(D11)
Mr = 470.26

211 mg of ligand (0.619 mmol) (C7) were stirred in 25 ml of n-butanol. 80 mg of CoCl$_2$ (0.619 mmol) were dissolved in 35 ml of n-butanol with heating and added to the solution, with the mixture spontaneously becoming blue. The mixture was subsequently refluxed for 24 hours. After refluxing for a number of hours, a bluish green solution was formed. The solvent was taken off in a high vacuum. The powder which remained was dried in a high vacuum for a number of hours. The complex was washed with absolute ether and dried again.

Appearance: green powder

Melting point: commencing at 100° C. and extending over a range of 30° C. without a color change.

Example D12

Synthesis of Complex (D12)

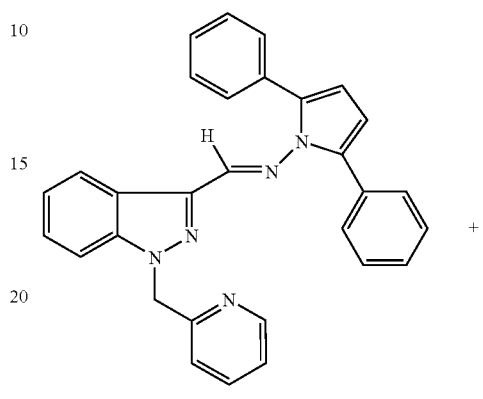

(C9)
$M_r = 453.55$

FeCl$_2$  $\xrightarrow{\text{n-BuOH}}$
$M_r = 126.75$

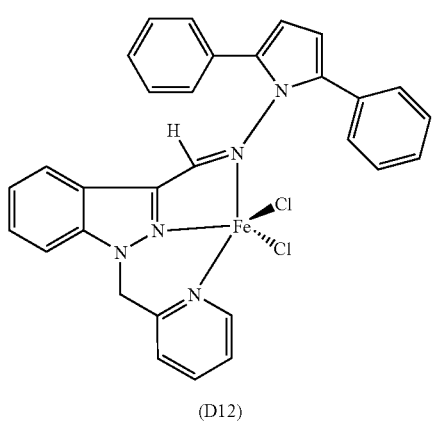

(D12)
$M_r = 580.30$ 205 mg of ligand (0.452 mmol) (C9) were stirred in 10 ml of n-butanol. 57 mg of FeCl$_2$ (0.452 mmol) were dissolved in 25 ml of n-butanol with heating and added to the solution, with the mixture becoming orange. After refluxing for one week, the solvent was taken off in a high vacuum. The powder which remained was dried in a high vacuum for a number of hours.

Appearance: ochre powder

Decomposition point: could not be determined precisely; everything was molten at T=136° C. and the color darkened

Example D13

Synthesis of Complex (D13)

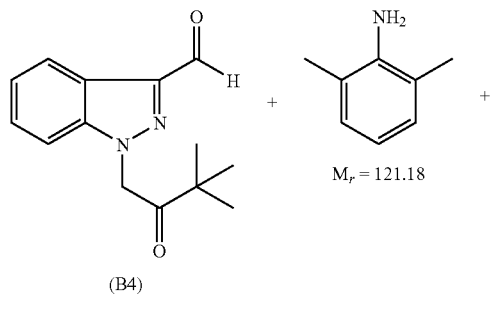

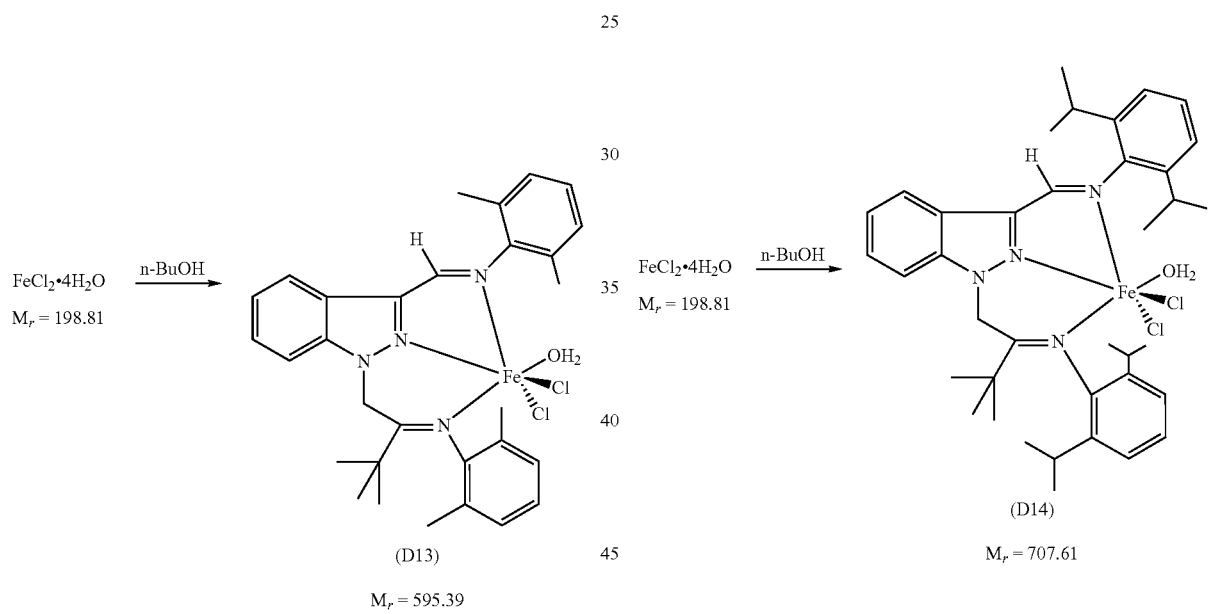

165 mg of keto component (0.675 mmol) (B4) were stirred in 20 ml of n-butanol by means of a magnetic stirrer. 134 mg of $FeCl_2 \cdot 4H_2O$ (0.675 mmol) were added and the reaction mixture was stirred at 85° C. on an oil bath for one hour. 167 μl of 2,6-dimethylaniline (1.35 mmol) were added by means of a syringe. Over a period of one hour, a color change from brown via green to blue was observed. The suspension was stirred at this temperature for 20 hours. The solvent was subsequently taken off in a high vacuum and the resulting powder was washed with hexane on a sintered glass suction filter and dried once again in a high vacuum. Yield 78%

Appearance: blue powder

Melting point: 108-109° C.

IR: 1583 cm$^{-1}$; 1627 cm$^{-1}$

Example D14

Synthesis of Complex (D14)

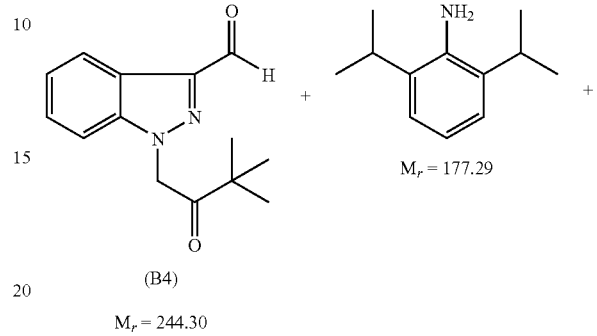

129 mg of keto component (0.530 mmol) (B4) were stirred in 20 ml of n-butanol by means of a magnetic stirrer. 105 mg of $FeCl_2 \cdot 4H_2O$ (0.530 mmol) were added and the reaction mixture was stirred at 85° C. on an oil bath for one hour. 200 μl of 2,6-diisopropylaniline (1.06 mmol) were added by means of a syringe. Over a period of one hour, a color change from brown via green to blue was observed. The suspension was stirred at this temperature for 20 hours. The solid was subsequently taken off in a high vacuum and the resulting powder was washed firstly with ether on a sintered glass suction filter. Since the precipitate was found to be readily soluble in ether, it was washed with hexane and dried once again in a high vacuum. Yield 67%

Appearance: blue powder

Melting point: 72-75° C.

IR: 1577 cm$^{-1}$; 1625 cm$^{-1}$

Example D15

Synthesis of Complex (D15)

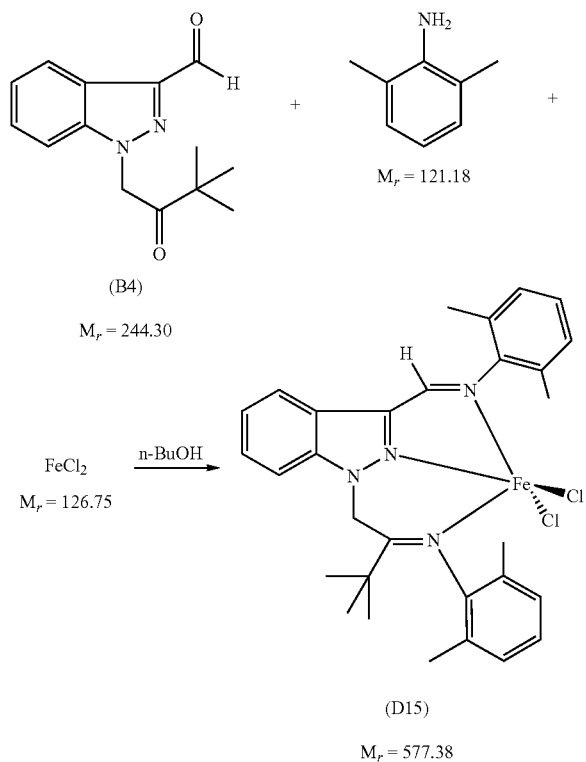

(D15)

$M_r = 577.38$ 150 mg of keto component (0.614 mmol) (B4) were stirred in 60 ml of n-butanol under an argon atmosphere by means of a magnetic stirrer. 65 mg of FeCl$_2$ (0.512 mmol) and 158 μl of 2,6-dimethylaniline (1.28 mmol) were added. The reaction mixture was heated at 80° C. on an oil bath. After stirring for 3 hours at this temperature, a yellowish orange solution was formed.

5 drops of glacial acetic acid were then added. After a further 15 hours, a dark green solution was formed. The solvent was taken off in a high vacuum, giving a shiny green solid. The residue was washed a total of three times with 35 ml each time of absolute ether and dried in a high vacuum.

Yield 57%
Appearance: greenish brown powder
Melting point: 150° C.
IR: 1588 cm$^{-1}$; 1604 cm$^{-1}$; 1724 cm$^{-1}$

Example D16

Synthesis of Complex (D16)

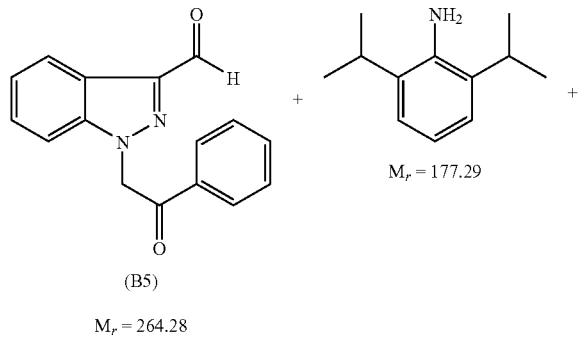

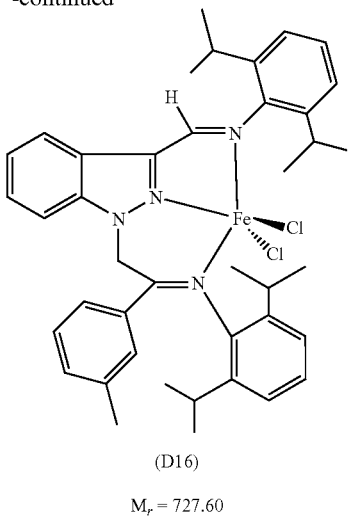

(D16)

$M_r = 727.60$ 102 mg of keto component (0.385 mmol) (B5) were stirred in 20 ml of n-butanol by means of a magnetic stirrer. 76 mg of FeCl$_2$*4H$_2$O (0.385 mmol) were added and the reaction mixture was heated at 85° C. on an oil bath. After 30 minutes, 146 μl of 2,6-diisopropylaniline (0.771 mmol) were added by means of a syringe. Over a period of one hour, the color changed from brown via green to blue. After a further 22 hours, a dark blue solution comprising a small amount of insoluble dark brown material was formed. The solvent was taken off in a high vacuum, giving a bluish green solid which was washed with hexane on a G4 sintered glass suction filter and dried again.

Yield 82%
Appearance: greenish blue powder
Melting point: 67-70° C.
IR: 1577 cm$^{-1}$; 1635 cm$^{-1}$ Polymerization The polymerization experiments were carried out in a 1 l four-neck flask provided with contact thermometer, stirrer with Teflon blade, gas inlet tube, condenser and heating mantle. 250 ml of toluene were placed in this flask, and the appropriate amounts of the complex were added at 40° C. under argon. The solution was subsequently heated at 75° C. for 10 minutes to bring all of the complex into solution. The solution was then cooled back down to 40° C. and the appropriate amount of 30% strength methylaluminoxane solution (MAO) in toluene from Crompton was added, as indicated in Table 1.

From 10 to 40 l/h of ethylene were passed through this solution, depending on the consumption. To stop the polymerization, the introduction of ethylene was stopped and argon was passed through the solution. The MAO was then decomposed completely by addition of a mixture of 15 ml of concentrated hydrochloric acid and 50 ml of methanol. After stirring for 15 minutes, 250 ml of methanol were added, resulting in the polymer formed being precipitated completely. The polymer was filtered off on a glass frit filter, washed three times with methanol and dried at 70° C. under reduced pressure. The polymerization data and product data are summarized in Table 1.

TABLE 1

| Example | Complex [μmol] | MAO [mmol] | Complex:Al | t(poly) [min] | Polymer [g] | Activity [kg$_{PE}$/(mol * h)] | [η] [dl/g] | $M_w$ | Q |
|---|---|---|---|---|---|---|---|---|---|
| P1 | (D8) 28.7 | 14.3 | 1:500 | 20 | 2.5 | 262 | 3.671 | 40 722 | 57.97 |
| P2 | (D9) 42.6 | 21.4 | 1:500 | 20 | 0.4 | 28 | 6.46 | 13 184 | 63.44 |
| P3 | (D10) 43.2 | 21.85 | 1:500 | 20 | 0.4 | 28 | 1.81 | 156 497 | 98 |

The invention claimed is:

1. A transition metal compound comprising a transition metal M and ligand L of the general structure:

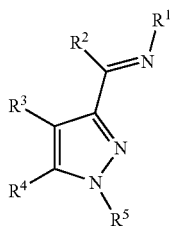

wherein $R^1$ is a $C_1$-$C_{40}$ radical; $R^2$ is hydrogen or a $C_1$-$C_{40}$ radical; $R^1$ and $R^2$ optionally form a ring system; and $R^1$, $R^2$, $R^3$, and $R^4$ optionally and independently comprise a heteroatom selected from N, O, P, S, As or Sb;

wherein $R^3$ and $R^4$ form a six-member ring and $R^5$ is selected from

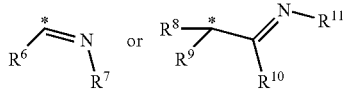

wherein $R^6$ and $R^{10}$ are independently hydrogen, $C_1$-$C_{12}$ alkyls, $C_6$-$C_{40}$ aryls, or $C_2$-$C_{40}$-heteroaromatic radicals containing O, N, or S; $R^7$ and $R^{11}$ are independently $C_1$-$C_{12}$ alkyls, $C_6$-$C_{40}$ aryls, or $C_2$-$C_{40}$ heteroaromatic radicals containing O, N, or S; $R^8$ and $R^9$ are independently hydrogen or a $C_1$-$C_{40}$ radical; $R^6$ and $R^7$ optionally form a ring system; and $R^{10}$ and $R^{11}$ optionally form a ring system; and wherein the transition metal compound has the general structure of $[LMX_nL^1_h]_m$, wherein M is Fe, Co or Ni; n is an integer from 1 to 4 m is an integer from 1 to 10, X are the same or different and are organic or inorganic radicals; two X radicals optionally form a divalent radical; $L^1$ is an uncharged ligand, and h is an integer from 0 to 4.

2. An olefin polymerization catalyst system comprising the transition metal compound of claim 1 and a cocatalyst.

3. The catalyst system of claim 2 which further comprises a support.

4. A process comprising polymerizing one or more olefins in the presence of the catalyst system of claim 2.

5. The process of claim 4 wherein the olefins are ethylene or α-olefins.

* * * * *